United States Patent
Krupenkin et al.

(10) Patent No.: US 10,938,276 B2
(45) Date of Patent: Mar. 2, 2021

(54) METHOD AND APPARATUS FOR MECHANICAL ENERGY HARVESTING USING VARIABLE INDUCTANCE MAGNETIC FLUX SWITCH

(71) Applicants: Thomas Nikita Krupenkin, Madison, WI (US); Joseph Ashley Taylor, Madison, WI (US)

(72) Inventors: Thomas Nikita Krupenkin, Madison, WI (US); Joseph Ashley Taylor, Madison, WI (US)

( * ) Notice: Subject to any disclaimer, the term of this patent is extended or adjusted under 35 U.S.C. 154(b) by 0 days.

(21) Appl. No.: 16/654,157

(22) Filed: Oct. 16, 2019

(65) Prior Publication Data

US 2020/0119619 A1    Apr. 16, 2020

Related U.S. Application Data

(60) Provisional application No. 62/745,993, filed on Oct. 16, 2018.

(51) Int. Cl.
*H02K 7/18*    (2006.01)
*F03G 5/06*    (2006.01)
(Continued)

(52) U.S. Cl.
CPC ............ *H02K 7/1876* (2013.01); *A61F 2/66* (2013.01); *F03G 5/06* (2013.01);
(Continued)

(58) Field of Classification Search
CPC . H02K 7/1876; F03G 5/06; A61F 2/66; A61F 2202/5072; A61F 2202/5073; A61F 2202/607; A61F 2202/6614
(Continued)

(56) References Cited

U.S. PATENT DOCUMENTS 3,696,251 A * 10/1972 Last ..................... H02K 35/00
                                                            290/53
3,824,512 A *  7/1974 Glass .................... H01H 35/32
                                                           335/205
(Continued)

FOREIGN PATENT DOCUMENTS

WO    2017030498    2/2017

OTHER PUBLICATIONS

Lecointe, Jean-Philippe et al., "Energy Harvesting from the External Magnetic Flux Generated by AC Electrical Rotating Machines", Przeglad Elektrotechniczy (Electrial Review), ISSN 0033-2097, R. 88 NR 7b/2012, pp. 94-97.

*Primary Examiner* — Pedro J Cuevas
(74) *Attorney, Agent, or Firm* — Wendy W. Koba

(57) ABSTRACT

A method of mechanical-to-electrical energy conversion utilizes a mechanical spring in combination with a rapid-action variable inductance magnetic flux switch to convert a spring-loaded mechanical energy into a change in magnetic flux captured by an electrical coil element within the magnetic flux switch. The change in coil inductance and magnetic flux induces a current to flow through the electrical coil in the form of a a pulse of electrical energy that may be stored. The electrical coil is coupled to the mechanical spring so that each time the spring is released, the coil moves with respect to a magnetic core and a change in flux is created. The application of an external mechanical force (such as human locomotion) functions to compress and subsequently "unlock" the mechanical switch, allowing for the electrical energy associated with the application of aperiodic forces to be harvested.

21 Claims, 20 Drawing Sheets

(51) Int. Cl.
*A61F 2/66* (2006.01)
*A61F 2/50* (2006.01)
*A61F 2/60* (2006.01)

(52) U.S. Cl.
CPC ............... *A61F 2002/5072* (2013.01); *A61F 2002/5073* (2013.01); *A61F 2002/607* (2013.01); *A61F 2002/6614* (2013.01)

(58) Field of Classification Search
USPC .................................................. 290/1 E, 1 R
See application file for complete search history.

(56) References Cited

U.S. PATENT DOCUMENTS

| | | | | |
|---|---|---|---|---|
| 3,898,403 A * | 8/1975 | Grayson | ............... | H01H 35/34 200/83 Q |
| 4,086,550 A * | 4/1978 | Conner | ............... | H01H 50/326 335/132 |
| 4,295,118 A * | 10/1981 | Herr | ............... | H03K 17/9517 323/294 |
| 4,327,344 A * | 4/1982 | Luckenbach | ............ | H01F 7/124 335/253 |
| 4,614,875 A * | 9/1986 | McGee | ............... | H02K 7/1853 290/1 C |
| 5,347,186 A * | 9/1994 | Konotchick | ......... | H02K 7/1876 310/17 |
| 6,994,450 B2 | 2/2006 | Mah | | |
| 7,157,653 B1 * | 1/2007 | Cahill | ............... | H01H 5/02 200/82 E |
| 7,231,874 B2 * | 6/2007 | Rastegar | ............... | F41H 11/02 102/207 |
| 7,285,868 B2 * | 10/2007 | Wilson | ............... | B60C 23/041 290/1 R |
| 7,304,398 B1 * | 12/2007 | Kim | ............ | F03G 7/00 290/1 E |
| 7,476,984 B2 * | 1/2009 | Kim | ............ | F03G 7/08 290/1 E |
| 7,569,952 B1 | 8/2009 | Bono et al. | | |
| 7,605,482 B2 * | 10/2009 | Brown | ............... | F03G 7/08 290/1 R |
| 7,626,279 B2 * | 12/2009 | Brown | ............... | F03G 7/08 290/1 R |
| 7,847,421 B2 * | 12/2010 | Gardner | ............... | F03G 7/08 290/1 R |
| 7,989,971 B2 * | 8/2011 | Lemieux | ............... | H02K 35/02 290/1 R |
| 8,030,786 B2 * | 10/2011 | Jackson | ............... | F03G 7/08 290/1 R |
| 8,183,746 B2 * | 5/2012 | Rastegar | ............... | F42C 11/008 310/339 |
| 8,217,523 B2 * | 7/2012 | Brown | ............... | H02K 7/1853 290/1 R |
| 8,350,394 B2 * | 1/2013 | Cottone | ............... | H02K 35/02 290/1 R |
| 8,390,137 B2 * | 3/2013 | Bryfogle | ............... | H02K 7/1876 290/1 R |
| 8,629,572 B1 * | 1/2014 | Phillips | ............... | H02K 7/1876 290/53 |
| 8,659,176 B2 * | 2/2014 | Hanchett, Jr. | ............. | F03G 7/08 290/1 R |
| 8,736,088 B2 * | 5/2014 | Kemball-Cook | ......... | F03G 7/08 290/1 R |
| 8,946,919 B2 * | 2/2015 | Phillips | ............... | H01F 7/0273 290/53 |
| 8,946,920 B2 * | 2/2015 | Phillips | ............... | H01F 7/0273 290/53 |
| 8,952,560 B2 * | 2/2015 | Phillips | ............... | H02K 35/02 290/53 |
| 8,963,358 B2 * | 2/2015 | Phillips | ............... | F03B 13/188 290/53 |
| 9,252,648 B2 * | 2/2016 | Furukawa | ............... | H02K 35/00 |
| 9,366,234 B2 * | 6/2016 | Sanchez | ............... | F03D 9/11 |
| 9,476,400 B2 * | 10/2016 | Phillips | ............... | H02K 35/02 |
| 9,644,601 B2 * | 5/2017 | Phillips | ............... | H02M 7/064 |
| 9,653,980 B2 | 5/2017 | Laurent | | |
| 9,913,321 B2 * | 3/2018 | Hotto | ............... | H05B 6/108 |
| 10,003,240 B2 * | 6/2018 | Rastegar | ............... | H02K 7/1853 |
| 10,011,910 B2 * | 7/2018 | Phillips | ............... | H02K 7/1876 |
| 10,175,306 B1 | 1/2019 | Miesner | | |
| 2004/0100100 A1 * | 5/2004 | Wilson | ............... | F03G 7/08 290/1 R |
| 2004/0113731 A1 * | 6/2004 | Moyer | ............... | H01F 7/1615 335/220 |
| 2005/0046531 A1 * | 3/2005 | Moyer | ............... | F01L 9/04 335/256 |
| 2008/0036307 A1 * | 2/2008 | Lu | ............... | H02K 35/04 310/15 |
| 2008/0164701 A1 * | 7/2008 | Brown | ............... | F03G 7/08 290/1 E |
| 2008/0164702 A1 * | 7/2008 | Brown | ............... | H02K 35/02 290/1 E |
| 2008/0174120 A1 * | 7/2008 | Gardner | ............... | F03G 7/08 290/1 C |
| 2009/0096219 A1 | 4/2009 | Annis et al. | | |
| 2009/0152990 A1 * | 6/2009 | Brown | ............... | F03G 5/06 310/339 |
| 2010/0045119 A1 * | 2/2010 | Jackson | ............... | F03G 7/08 310/20 |
| 2010/0236440 A1 * | 9/2010 | Rastegar | ............... | F42C 11/02 102/209 |
| 2010/0314961 A1 | 12/2010 | An et al. | | |
| 2011/0074162 A1 * | 3/2011 | Cottone | ............... | H02K 35/02 290/1 R |
| 2011/0080005 A1 * | 4/2011 | Bryfogle | ............... | H02K 7/1876 290/1 A |
| 2012/0133466 A1 | 5/2012 | Pedersen | | |
| 2013/0313838 A1 * | 11/2013 | Sakamoto | ............... | H02K 33/18 290/1 R |
| 2014/0117673 A1 * | 5/2014 | Phillips | ............... | F03B 13/1855 290/53 |
| 2014/0117674 A1 * | 5/2014 | Phillips | ............... | H02M 7/066 290/53 |
| 2014/0117785 A1 * | 5/2014 | Furukawa | ............... | H02K 35/00 310/15 |
| 2014/0313001 A1 * | 10/2014 | Phillips | ............... | H02K 35/02 335/306 |
| 2014/0339928 A1 * | 11/2014 | Phillips | ............... | F03B 13/1855 310/30 |
| 2015/0145258 A1 * | 5/2015 | Phillips | ............... | F03B 13/16 290/53 |
| 2015/0330372 A1 * | 11/2015 | Nulman | ............... | H02K 35/02 290/1 R |
| 2016/0010619 A1 * | 1/2016 | Phillips | ............... | H01F 7/0273 290/53 |
| 2016/0020671 A1 * | 1/2016 | Rastegar | ............... | H02K 7/1853 290/1 E |
| 2017/0198401 A1 * | 7/2017 | Phillips | ............... | C23F 13/005 |
| 2018/0202420 A1 * | 7/2018 | Wong | ............... | F03G 5/06 |
| 2019/0087063 A1 * | 3/2019 | Gomi | ............... | H02K 7/1876 |
| 2019/0207492 A1 | 7/2019 | Lin et al. | | |

\* cited by examiner

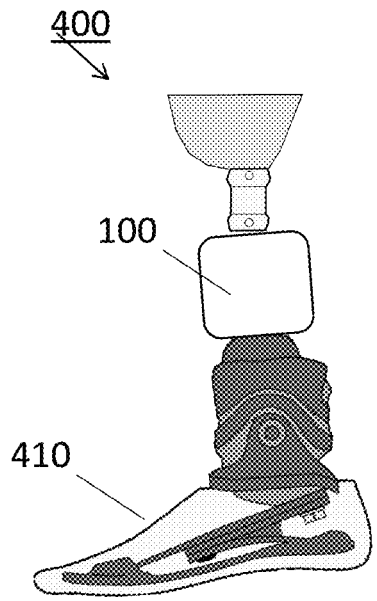
FIG. 26
FIG. 27
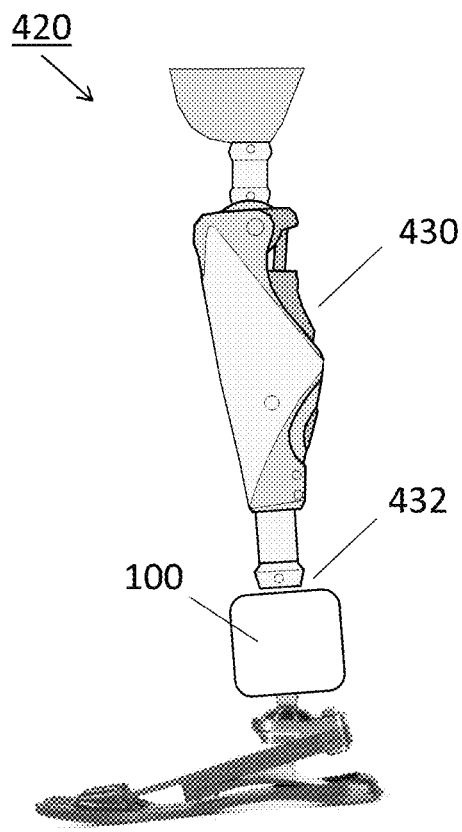

METHOD AND APPARATUS FOR MECHANICAL ENERGY HARVESTING USING VARIABLE INDUCTANCE MAGNETIC FLUX SWITCH

CROSS-REFERENCE TO RELATED APPLICATIONS

This application claims the benefit of U.S. Provisional Application No. 62/745,993, filed Oct. 16, 2018, and herein incorporated by reference.

TECHNICAL FIELD

The present invention relates to mechanical energy harvesting and, more particularly, to the utilization of a variable inductance magnetic flux switch to convert mechanical energy (e.g., spring force) into electrical energy that can be stored for later use as needed.

BACKGROUND OF THE INVENTION

Currently, the majority of autonomous and mobile electronic systems are powered by electrochemical batteries. Although the battery quality has substantially improved over the last two decades, their energy density has not greatly increased. At present, factors such as cost, weight, limited service time, and waste disposable problems (all intrinsic to the materials used to create batteries) are impeding the advance of many areas of electronics. The problem is especially acute in the portable electronics space, where rapidly growing performance and sophistication of mobile electronic devices leads to ever-increasing power demands that electrochemical batteries are unable to meet.

One of the technologies that holds great promise to substantially alleviate today's reliance on electrochemical batteries is high-power energy harvesting. The concept of energy harvesting works towards developing self-powered devices that do not require replaceable power supplies. In cases where high mobility and high-power output is required, harvesters that convert mechanical energy into electrical energy are particularly promising as they can tap into a variety of high-power-density energy sources, including mechanical vibrations, human and machine motion, etc.

High-power harvesting of mechanical energy is a long-recognized concept which has not been commercialized in the past due to the lack of a viable energy harvesting technology. Existing methods of mechanical-to-electrical energy conversion such as electromagnetic, piezoelectric, or electrostatic do not allow effective direct coupling to the majority of high-power environmental mechanical energy sources. Bulky and expensive mechanical or hydraulic transducers are required to convert a broad range of aperiodic forces and displacements typically encountered in nature into a form accessible for conversion using those methods. Thus, any method of mechanical-to-electrical energy conversion that can provide effective coupling to a broad range of forces and displacements would be highly beneficial as it would allow energy harvesting to extend into a wider range of environments. Many practical applications would benefit from such energy conversion methods, including, for example, lower and upper limb prosthetic devices, energy harvesting from human motion, including human locomotion, internet-of-things devices, and the like.

SUMMARY OF THE INVENTION

The needs remaining in the art are addressed by the present invention, which relates to mechanical energy harvesting and, more particularly, to the utilization of a variable inductance magnetic flux switch, where magnetic flux is generated in response to the movement of a spring-loaded electrical coil through a magnetic field.

As described in detail below, the present invention is directed to a method of mechanical-to-electrical energy conversion utilizing an inventive apparatus comprising a mechanical energy storage device (such as a mechanical spring) that is used in combination with a rapid-action variable inductance magnetic flux switch to convert a spring-loaded mechanical energy into a change in magnetic flux that is converted into a pulse of electrical energy that may be stored.

In exemplary embodiments of the present invention, the variable inductance magnetic flux switch comprises a movable coil and a stationary magnetic core. The mechanical spring is used to control the movement of the coil with respect to the magnetic core so as to change the amount of magnetic flux captured by the coil as well as the coil inductance, the changes in flux and inductance inducing a current to flow through the coil, which exits the coil as a pulse.

Various embodiments may use a single magnetic core element, or a pair of oppositely-poled magnetic core elements to control the amount of energy that is harvested by the action of the mechanical spring. Different means for unlocking and re-locking the mechanical spring are proposed and used to allow the energy harvesting to proceed without the need for a separate process to re-start a subsequent energy collection cycle. Said another way, the actuation process is self-initiated by a resettable switching mechanism once the spring displacement or force exceeds a certain predefined value.

It is an aspect of the present invention that the use of a variable inductance magnetic flux switch, as described in detail below, provides effective coupling to a broad range of forces and displacements.

A method implemented in accordance with the present invention allows for many currently un-accessible mechanical energy sources to be involved in a process of conversion into electrical energy. The method of the present invention is particularly well-suited for extracting energy from sources characterized by relatively slow aperiodic motion with high forces and low displacements, such as those encountered in human locomotion and lower limb prosthetic devices.

An exemplary embodiment of the present invention takes the form of an apparatus for harvesting electrical energy from motion associated with mechanical energy, comprising a mechanical spring disposed within a housing; and a variable inductance magnetic flux switch positioned within an open central area of the housing. The variable inductance magnetic flux switch itself is formed to include a stationary magnetic core component and a movable electrical coil subassembly disposed to surround the stationary magnetic core component The movable electrical coil subassembly is coupled to the mechanical spring in a manner such that movement of the mechanical spring also provides movement of the electrical coil subassembly. A plunger is disposed over the combination of the stationary magnetic core component and the movable electrical coil subassembly, where the plunger is responsive to the application of an external force to move the variable inductance magnetic flux switch downward and into the housing and compressing the mechanical spring. The apparatus also includes a spring lock mechanism for releasing the mechanical spring when in a compressed state, providing movement of the mechanical spring and coupled electrical coil subassembly, where the movement of the electrical coil subassembly with respect to the stationary magnetic core creates a change in the magnetic flux captured by the electrical coil subassembly, as well as the coil subassembly inductance, and induces a flow of electrical current for storage as the output of the apparatus.

Yet another embodiment of the present invention may be defined in terms of a method of harvesting electrical energy from mechanical movement, comprising the steps of: (1) providing a variable inductance magnetic switch including a stationary magnetic core component and a movable electrical coil subassembly disposed to surround the stationary magnetic core component; (2) providing a mechanical spring coupled to the movable electrical coil; (3) impressing a force on the coupled mechanical spring and movable electrical coil so as compress the mechanical spring; and (4) unlocking the compressed mechanical spring to cause movement of the released mechanical spring and coupled electrical coil subassembly, where the movement of the electrical coil subassembly with respect to the stationary magnetic core creates a change in the magnetic flux captured by the electrical coil subassembly and the change in the coil inductance, thereby inducing a flow of electrical current therethrough.

Other and further embodiments of the present invention will become apparent during the course of the following discussion and by reference to the accompanying drawings.

BRIEF DESCRIPTION OF THE DRAWINGS

Referring now to the drawings, where like numerals represent like parts in several views:

FIG. 26 illustrates an application of the inventive harvesting apparatus as used in combination with a prosthetic foot device, providing electrical power to the device;

FIG. 27 illustrates an application of the inventive harvesting apparatus as used in combination with a prosthetic lower limb;

DETAILED DESCRIPTION

As mentioned above and will be described in detail below, the present invention relates to an apparatus and method for harvesting electrical energy from mechanical energy that utilizes a magnetic flux switch formed of a centrally-located magnetic core and an electrical coil disposed to surround the magnetic core. A mechanical spring is attached to a structure supporting the electrical coil and accumulates mechanical energy as it is compressed. When the tension force holding the spring in compression is overcome (i.e., the spring is "unlocked"), the electrical coil translates longitudinally with the respect to the magnetic core. The movement of the electrical coil with respect to the stationary magnetic core is sufficient to change the amount of magnetic flux captured by coil and thus induce an electric current to flow within the coil. This current (typically in the form of pulses) may then be immediately used, or stored in a battery/capacitor for later use, as needed.

The inventive apparatus operates on the application of an external force to both compress the mechanical spring and then "unlock" the compressed spring to initiate the movement of the electrical coil. Therefore, a relatively slow, aperiodic motion involving a high magnitude force with minimal displacement is contemplated as able to control the inventive apparatus and generate electrical energy in response to this motion. Indeed, It is contemplated that human motion is one exemplary mechanical force that may be applied to the mechanical spring to initiate the operation of the inventive apparatus. Besides the inducement of an electric current by the change in flux passed through the coil area, the change in the coil's inductance as a function of its movement with respect to the magnetic core is a second mechanism that also induces the flow of current through the coil.

Figure 1:
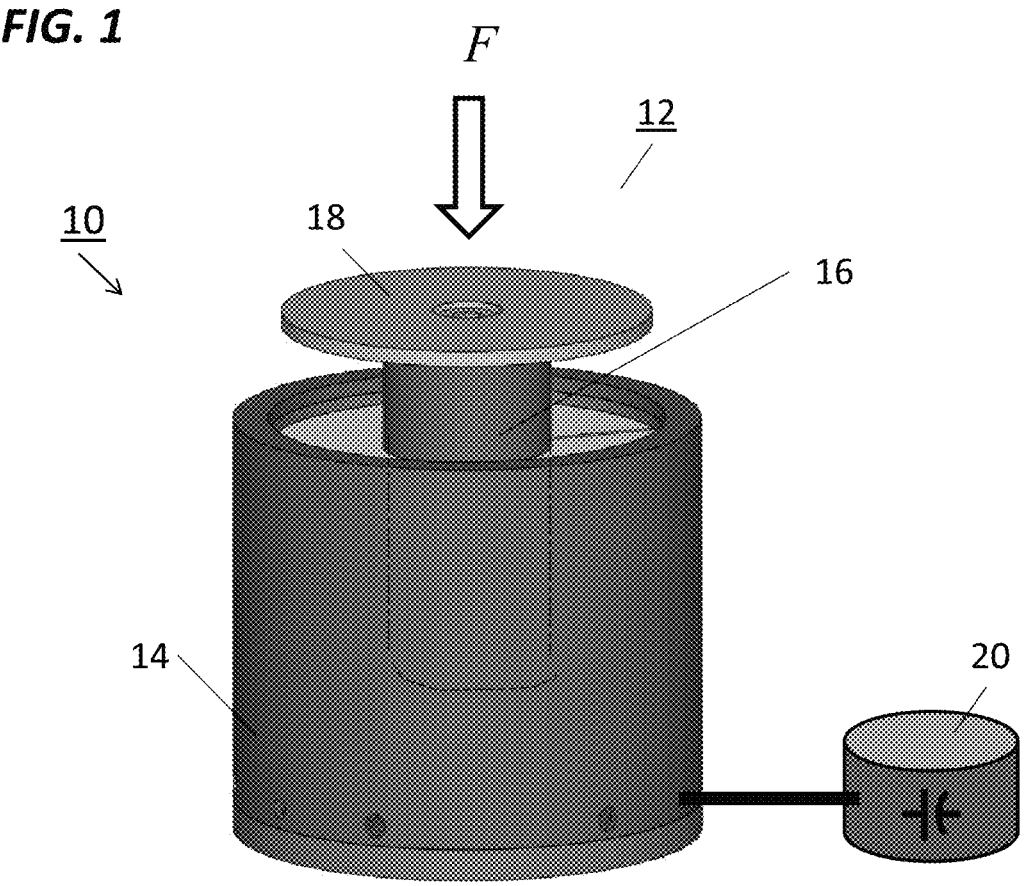
FIG. 1 is an external view of mechanical energy harvesting apparatus formed in accordance with the present invention.
Figure 2:
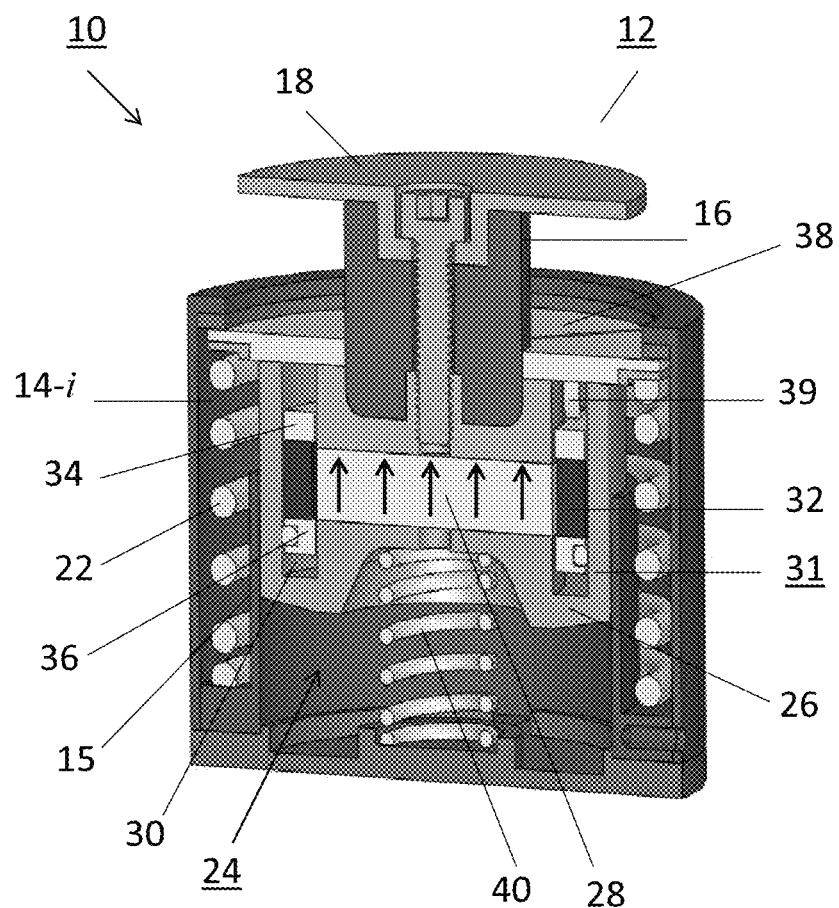
FIG. 2 is a cross-sectional view of the apparatus of FIG. 1.

FIG. 1 is an external view of an exemplary energy harvesting apparatus 10 formed in accordance with one exemplary embodiment of the present invention, with FIG. 2 being a cross-sectional view that illustrates the various internal components utilized to form a variable inductance magnetic flux switch within apparatus 10. Referring to FIG. 1, energy harvesting apparatus 10 is shown as comprising a plunger 12 to which an external actuation force F can be applied, and a housing 14 that encases the remaining components of the apparatus as will be discussed in detail below. Plunger 12 includes a cylindrical base element 16 and a plate 18 positioned above base element 16 as shown. Plunger 12 is configured to move up and down in a central opening of housing 14 in a manner such that the application of an external force to plunger 12 causes it be pressed downward into housing 14. As discussed in detail below, plunger 12 supplies a spring-loaded mechanical force, which is thereafter overcome such that plunger 12 is moved by spring action back in the opposite direction out of housing 14. It is this latter movement of plunger 12 that induces the flow of electrical current, which exits housing 14 as shown and is collected by an external electrical energy storage device 20 (which may comprise a capacitor or other suitable means). Plunger 12 is pressed downward time and again, with each action of its movement inducing the flow of electricity through an included coil.

Figure 3:
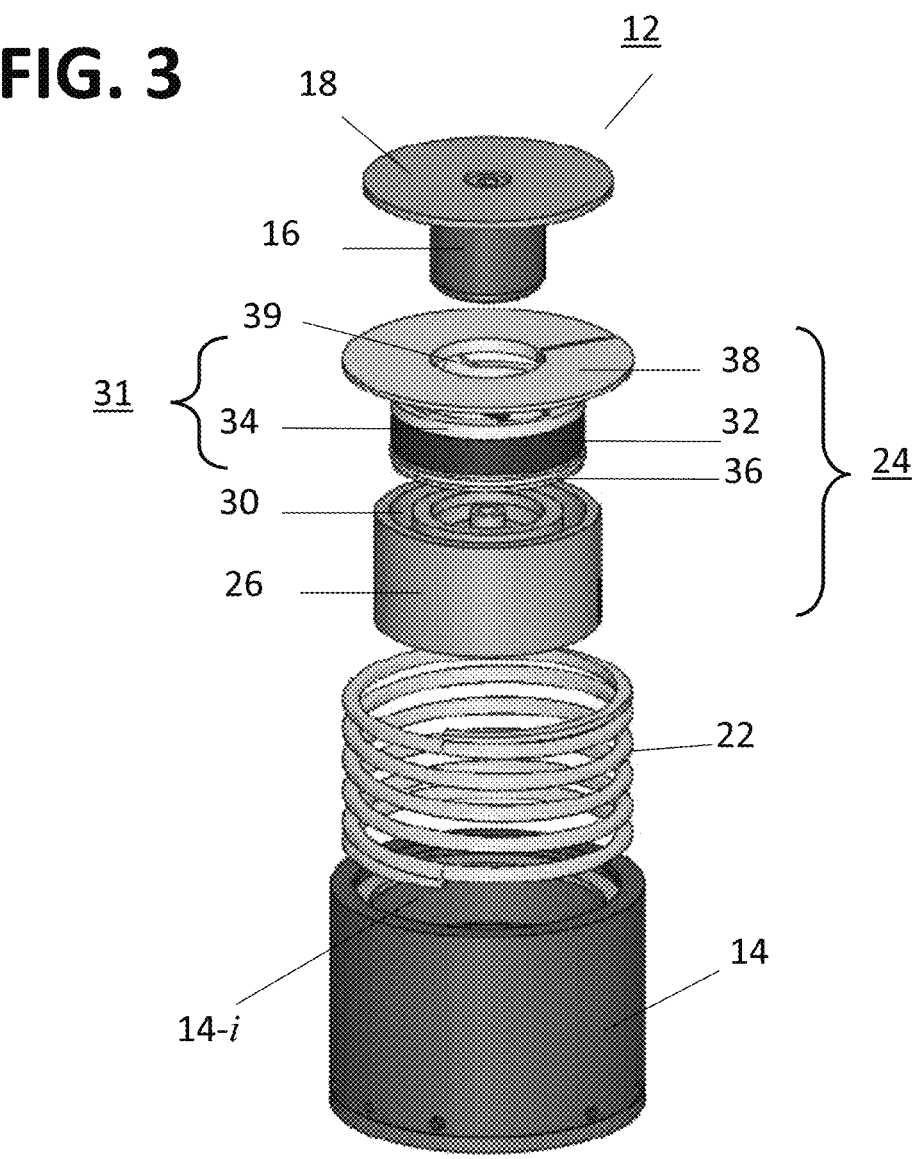
FIG. 3 is an exploded view of the various components forming the apparatus shown in FIGS. 1 and 2.

FIG. 2 presents a cross-sectional view of apparatus 10, showing both plunger 12 and housing 14, as well as a mechanical spring 22 and a variable inductance magnetic flux switch 24 (hereinafter referred to as "flux switch 24" for the sake of brevity). FIG. 3 is an exploded view of various components within apparatus 10, where it is useful to refer to both FIGS. 2 and 3 for an understanding of the method of providing energy harvesting by apparatus 10. In general and in accordance with the principles of the present invention, energy harvesting occurs through the action of flux switch 24 to convert the movement of mechanical spring 22 into electrical energy that may be stored (using storage device 20 as shown in FIG. 1, for example) and thereafter accessed as needed.

Referring to both FIGS. 2 and 3, mechanical spring 22 is shown as disposed within housing 14 so as encircle an inner periphery 14-$i$ of the exterior wall of housing 14 and allow the interior portion of the assembly to remain vacant for the subsequent location of the various components of flux switch 24. The particular embodiment of the present invention shown in FIGS. 2 and 3 utilizes a "magnetic lock" to control the release of mechanical spring 22. An interior wall segment 15 (concentric with housing 14) is included in this embodiment and used as an element of this magnetic lock action (as will be described in more detail below in association with FIGS. 6 and 7).

Continuing with reference to FIGS. 2 and 3, flux switch 24 itself is shown as comprising a cylindrical ferromagnetic shell 26 formed to include a centrally-located magnetic core 28 (which comprises a permanent magnet component). Shell 26 also includes a trench 30 located in proximity to its outer wall, where trench 30 is sized to accommodate the remaining components of magnetic flux switch 24 in a manner where these components may be moved up and down within trench 30 of shell 26, under the control of the movement of spring 22, as described below.

The remaining components of magnetic flux switch 24 comprise a movable subassembly 31, including an electrical coil 32 that is disposed between a pair of ferromagnetic rings 34, 36. It is this subassembly 31 that is positioned within trench 30 and is able to move up and down along trench 30 (as mechanical spring 22 moves, described below). A ferromagnetic lock plate 38 and a plurality of vertical attachment pins 39 comprise the physical support for coil 32 and rings 34, 36, and terminates as a circular ferromagnetic disk that is attracted to (and thus capable of being dis-engaged from) shell 26. As best shown in FIG. 2, lock plate 38 extends outward toward the periphery of housing 14 so as to at least cover mechanical spring 22. The downward movement of lock plate 38 (via attached plunger 12) thus functions to compress mechanical spring 28 into the space between housing 14 and interior wall segment 15.

In accordance with this particular embodiment of the present invention, the magnetic attachment between lock plate 38 and shell 26 forms the magnetic lock mechanism. As will be discussed below, the contact between lock plate 38 and interior side wall 15 functions to dis-engage lock plate 38 from shell 26 such that the compressed mechanical spring 22 is "unlocked" and permitted to return to its de-compressed state.

Also shown in FIG. 2 is a return spring 40, disposed within a central area of housing 14 below shell 26. As will be discussed below, return spring 40 (or a similar mechanism) is utilized in accordance with the present invention to re-set the position of plunger 12 to extend above housing 14 at the end of an energy conversion cycle so that plunger 12 is automatically in position to begin the next cycle of the harvesting of mechanical energy.

Figure 4:
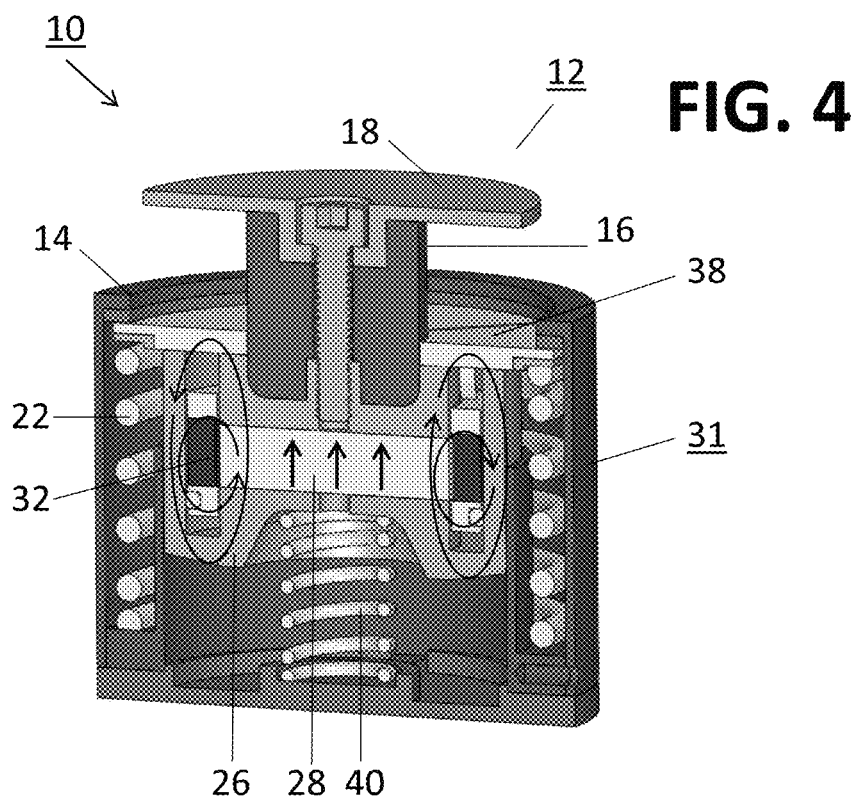
FIG. 4 shows the inventive energy harvesting apparatus in its initial "rest" state, prior to the application of an external force.
Figure 5:
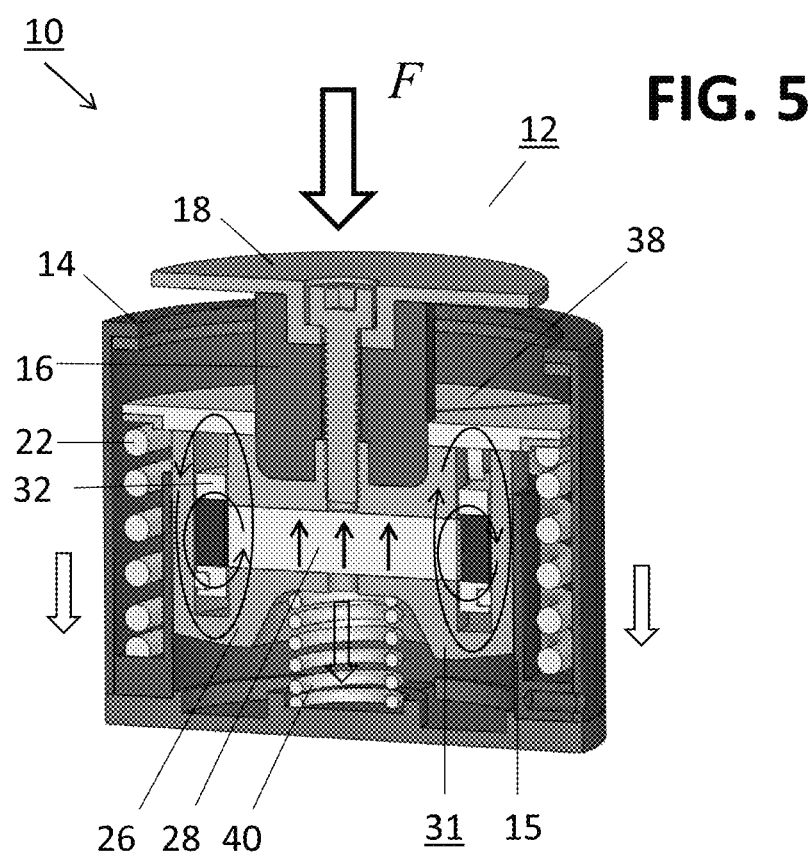
FIG. 5 illustrates a following step in the process of using the inventive apparatus, where an external force is applied to the apparatus.
Figure 6:
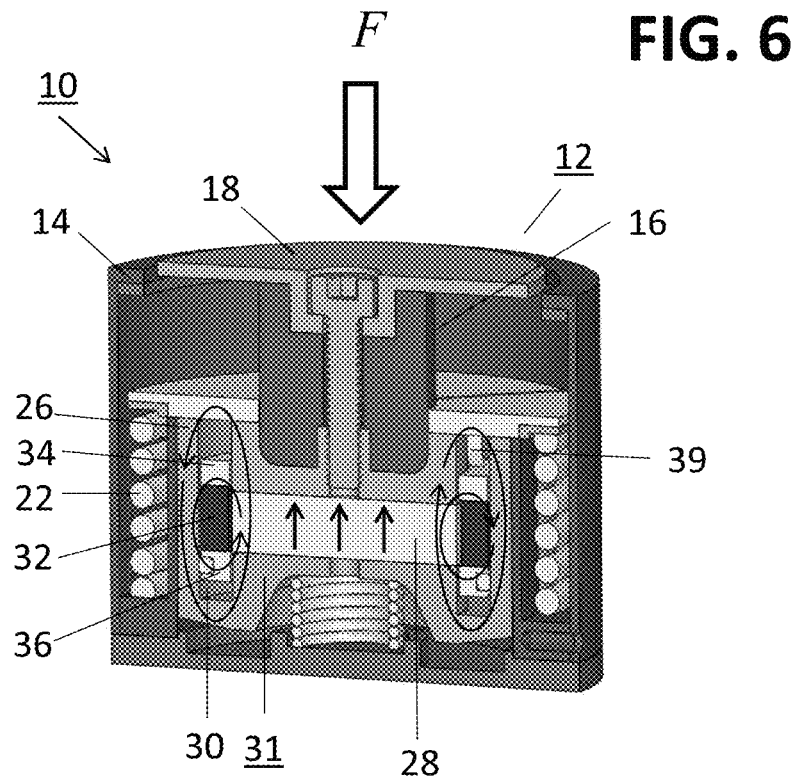
FIG. 6 shows the apparatus at a point in the process where the mechanical spring included within the energy harvesting apparatus is fully compressed.
Figure 7:
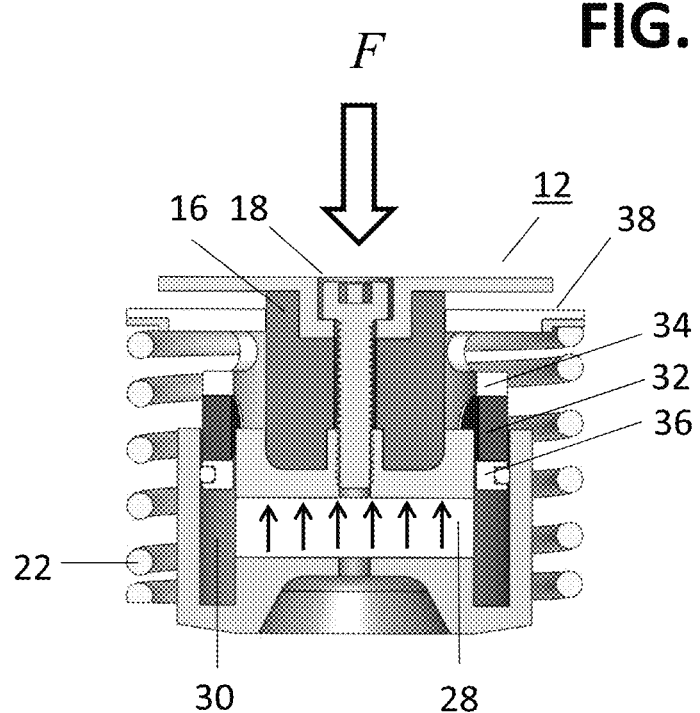
FIG. 7 is a simplified drawing of the flux switch portion of the inventive apparatus, illustrating the relative motion of the electrical coil with respect to the magnetic core upon "unlocking" of the compressed spring.
Figure 8:
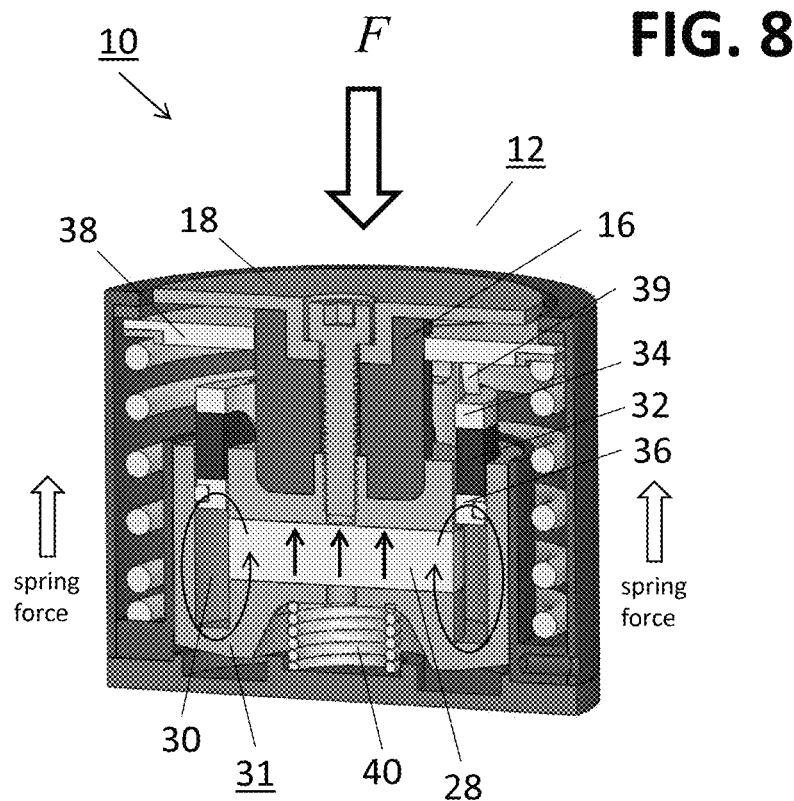
FIG. 8 shows a following position of the inventive apparatus where the mechanical spring has been fully de-compressed.
Figure 9:
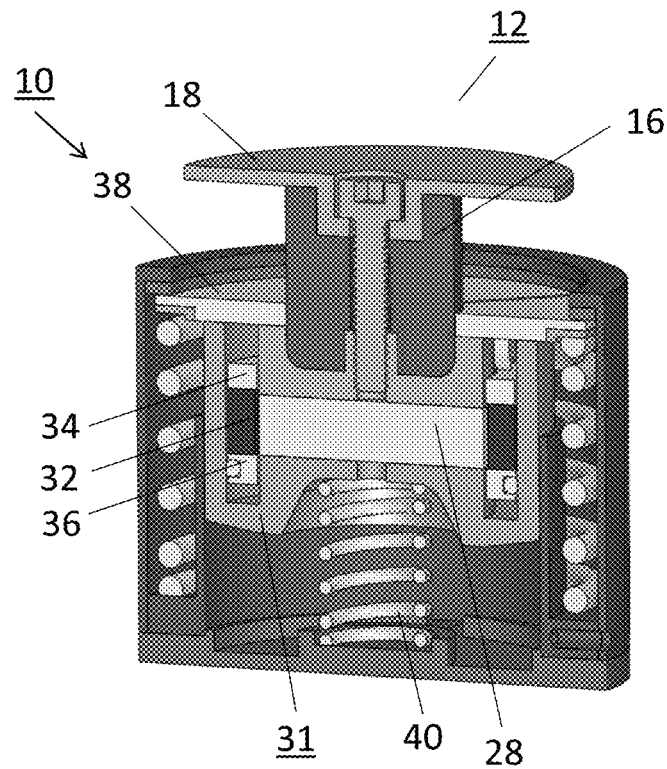
FIG. 9 illustrates the apparatus at a following point in time where the external force has been removed.

FIGS. 4-9 schematically illustrate the operation of this exemplary embodiment of the inventive apparatus for converting mechanical energy into electrical energy. The apparatus is shown in five stages of operation, as follows: FIG. 4 illustrates apparatus 10 in a "ready" for actuation state (i.e., prior to the application of an external force to plunger 12); FIG. 5 illustrates apparatus 10 in a "mechanical force" generation state (i.e., the application of an external force to plunger 12 to compress spring 22); FIG. 6 illustrates apparatus 10 in a "fully compressed" spring state, at a point in time where spring 22 is first unlocked; FIG. 7 illustrates an initial release state (i.e., with mechanical spring 22 starting to return to its initial state, also moving subassembly 31 upward within trench 30 of shell 26 and away from magnetic core 28); FIG. 8 illustrates a fully released state; and FIG. 9 illustrates a final step of the removal of the external force, allowing return spring 40 to move plunger 12 back to its initial position. The details of each state of operation, particularly as it impacts the change in magnetic flux captured by coil 32 will now be discussed in detail below.

Referring initially to FIG. 4, apparatus 10 is shown in this initial state with no external force applied to plunger 12. Shown in this view is the direction of the magnetic field through magnetic core 28, with the flux lines circling as shown around electrical coil 32. The captured flux remains constant as long as no external force is applied, and spring 22 remains fully expanded in its location between housing 14 and lock plate 38. In this initial state, electrical coil 32 is defined as exhibiting both a maximum flux and a maximum inductance. Since a substantial portion of the total magnetic flux flows through plunger 12, this allows for plunger 12 to be strongly attracted to shell 26. This attraction enables the magnetic lock action, as mentioned above, which keeps plunger 12 attached to shell 26.

FIG. 5 illustrates a next step in the inventive method of harvesting electrical energy from mechanical energy. As shown, an external force F is applied to plunger 12, which begins to compress spring 22 so that it begins to accumulate mechanical energy. At this point, lock plate 38 is still engaged with shell 26 (via the magnetic attraction between the two elements). As long as plate 38 and shell 26 remain joined, there is no relative movement between coil 32 and magnetic core 28 and, therefore, no change in the flux captured by coil 32. Thus, at this point in the process, there is not yet any creation of electrical energy, only the continued accumulation of mechanical energy.

FIG. 6 illustrates the point in the process where mechanical spring 22 is fully compressed in the space between the outer portion of housing 14 and interior wall segment 15 with lock plate 38 still preventing the release of mechanical spring 22. As shown, under the continued application of an external force, lock plate 38 now comes into connect with a top surface of interior wall segment 15, which functions as a mechanical "stop" and presents any further downward movement of plate 38. Therefore, since an external force continues to be applied to plunger 12, at some point in time this force will overcome the magnetic attraction between plate 38 and shell 26, causing shell 26 to break contact and continue to move downward. The separation of lock plate 38 from shell 26 functions to "open" the magnetic lock, releasing fully-compressed mechanical spring 22. As shown below, the unlocking allows for subassembly 31 (consisting of of coil 32, plugs 34, 36, plate 38 and vertical attachment pins 39) to also be moved upward within trench 30 of shell 26 by the force of mechanical spring 22.

FIG. 7 is a simplified diagram of flux switch 24 at the point in time when lock plate 38 begins to move upwards under the control of the motion of mechanical spring 22. Inasmuch as lock plate 38 is a component of movable subassembly 31 including coil 32, the upward movement of lock plate 38 also causes coil 32 to move upward and thus begin to shift its position with respect to stationary magnetic core 28. The change in position between these two elements thus creates a change in the magnetic flux captured by coil 32, inducing a flow of current through coil 32. The induced current will continue to be created as along as the flux density associated with coil 32 continues to change (i.e., as coil 32 and magnetic core 28 continue to separate by the upward movement of coil 32). Thus, in accordance with the teachings of the present invention, the unlocking of compressed mechanical spring 22 initiates the process of converting mechanical energy to electrical energy, the spring force moving coil 32 with respect to magnetic core 28 to induce a current to flow through coil 32.

In embodiments where flux switch 24 is configured to have a range of motion sufficient to allow coil 32 to be fully lifted out of shell 26, there will no longer be any magnetic flux that is captured by coil 32 once is it fully separated from shell 26 and away from its magnetic field. It is at this point in time that the coil inductance also drops to its lowest value (since it is no longer embedded within shell 26). As mentioned above, this abrupt decrease in coil inductance also generates the flow of electrical current through coil 32.

In particular, current will continue to flow until lock plate 38 comes into contact with plunger 12 (which is still under force), as shown in FIG. 8. As long as an external force remains applied to this configuration, flux switch 24 remains stable, with no relative movement between coil 32 and magnetic core 28 and, therefore, no further generation of electrical energy.

At some point in time, the external force is removed and return spring 40 is able to release, as shown in FIG. 9, returning plunger 12 and attached shell 26 (including associated magnetic core 28) to the initial position. As shell 26 transitions from the arrangement of FIG. 8 to that of FIG. 9, an additional current is generated as the flux again goes through another change. However, in this direction the coil inductance is working against the direction of flow of the induced current, so a smaller magnitude of current is created. Apparatus may remain in this state indefinitely, yet ready to begin the next harvesting cycle as soon as an external force is re-applied to plunger 12. The ability to remain in the state as shown in FIG. 9 is an advantage of the inventive apparatus when used to harvest aperiodic forces.

Summarizing, with electrical coil 32 and ferromagnetic plugs 34, 36 forming a subassembly disposed to move up and down within trench 30 of shell 26, the achievable separation between electrical coil 32 and magnetic core 28 controls how much energy is generated. In configurations where coil 32 is able to be completely displaced from shell 26, a maximum amount of energy is generated.

While optimum in terms of generating maximum electrical energy, the requirement of providing full separation between coil 32 and shell 26 is difficult to obtain in manufacture. Thus, other configurations of this embodiment may be preferred where the movement of coil 32 is somewhat limited (e.g., coil 32 does not complete exit shell 26). Additionally, it is possible to remove switch plugs 34, 36 from the configuration to simply the fabrication process. The elimination of plugs 34, 36, however, makes the change in captured flux much less abrupt and, as a result, significantly less electrical energy is generated in this arrangement.

Electrical energy generation in accordance with the present invention is actually associated with two different mechanisms. The first mechanism is the change in magnetic flux captured by coil 32, as discussed above. The faster coil 32 moves with respect to magnetic core 28, the more electrical energy is generated. The second mechanism by which electrical energy is generated is the related decrease in the inductance of coil 32 itself when it is energized, as mentioned above. Again, the faster the decrease, the more energy that is generated. However, as noted above this latter component works against energy generation during the "return" trip from the position of FIG. 8 to that of FIG. 9. While there is still a change in magnetic flux that induces a current, the coil inductance is actually increasing as a result in the change of sign, thus working against energy generation.

Since these final steps of re-setting plunger 12 constrains the amount of energy that may be generated, the embodiment of the present invention discussed thus far may not be particularly well-suited to support energy generation in systems where oscillatory motion of a mechanical component (spring) is available and useful for energy harvesting. That is, if all of the available mechanical energy cannot be converted to electrical energy during a single cycle of movement through the states shown in FIGS. 4-9, the unused mechanical energy (i.e., the additional oscillations of spring 22) will be dissipated as heat.

Figure 10:
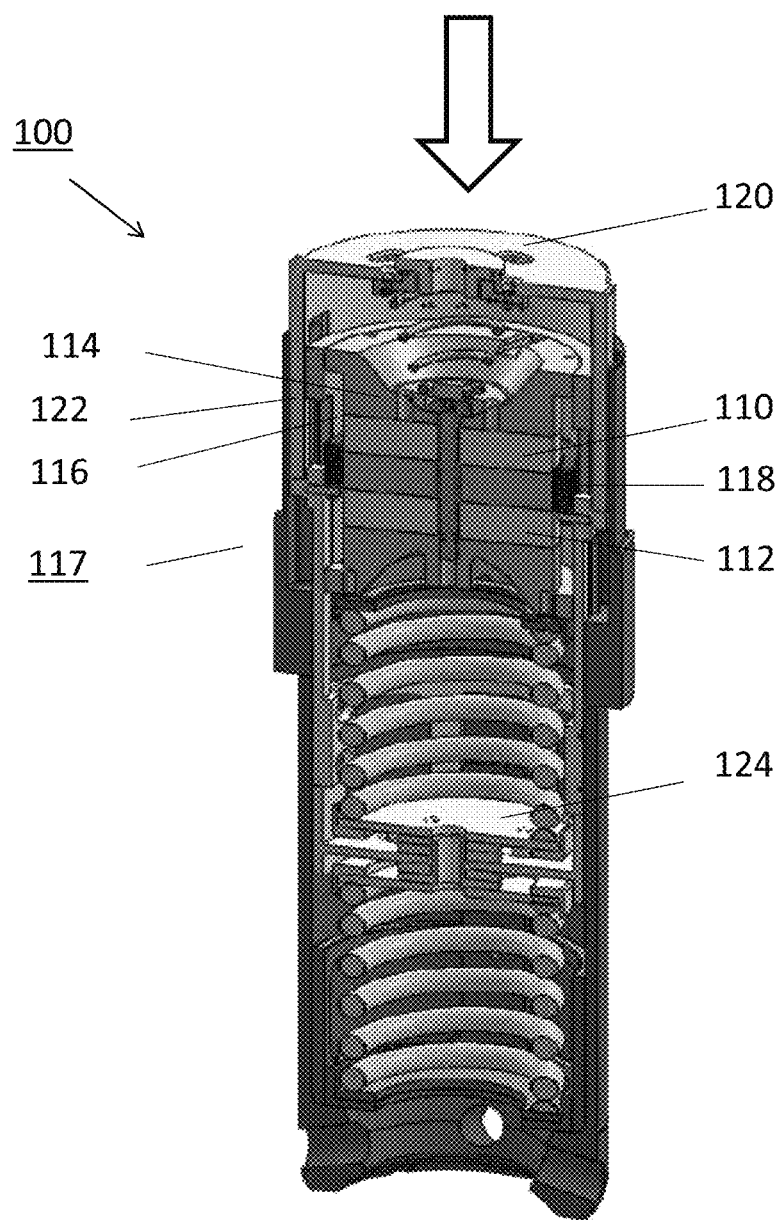
FIG. 10 illustrates an another embodiment of the present invention, referred to as a "dual-core" embodiment, including the use of a pair of magnetic core elements.

FIG. 10 illustrates another embodiment of the present invention, referred to as a "dual-core" energy harvesting apparatus 100. Here, a pair of oppositely-poled first and second magnetic core elements 110, 112 is disposed within a shell 114 and positioned such that there is an intermediate portion of the ferromagnetic material of shell 114 separating first magnetic core 110 from second magnetic core 112. As with the single-core embodiment discussed above, shell 114 includes a trench 116, with a movable subassembly 117 comprising at least an electrical coil 118 positioned within trench 116.

Figure 11:
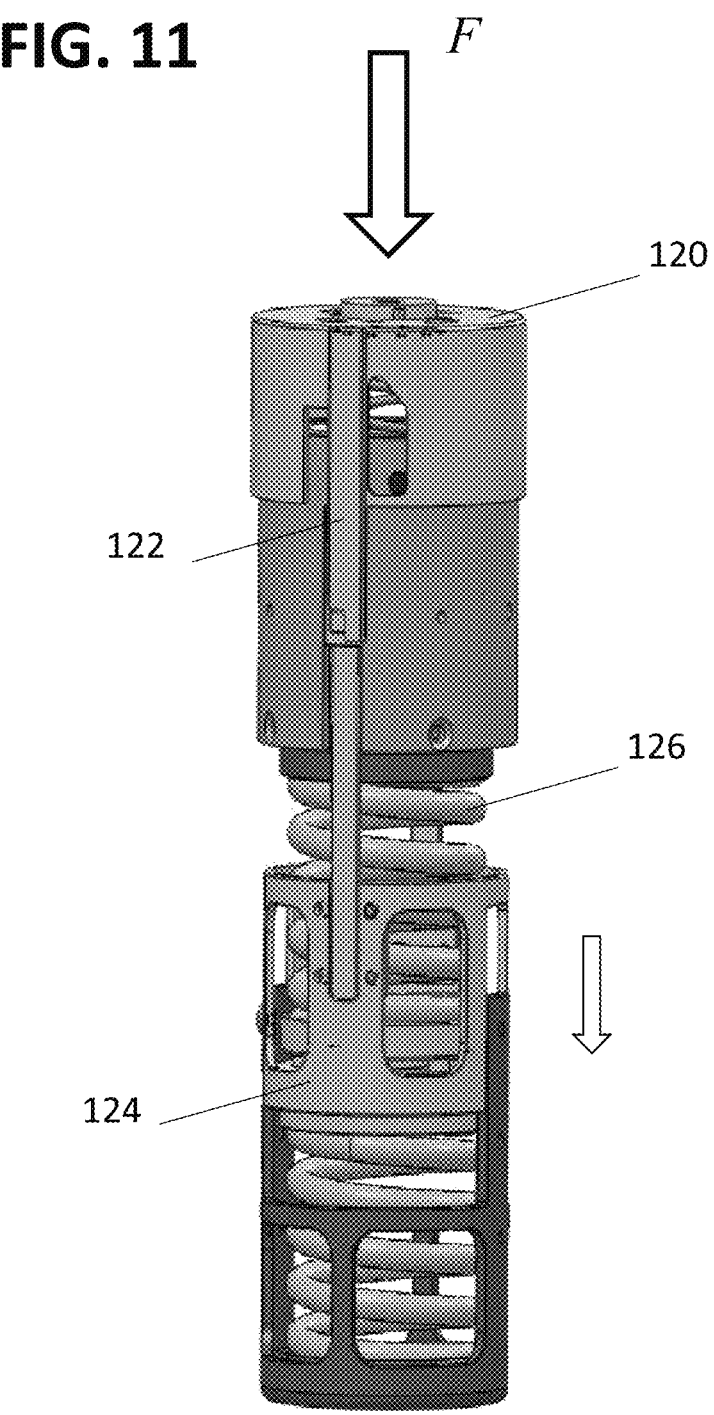
FIG. 11 shows the application of an external force and the movement of a locking cap on the dual-core energy harvesting apparatus of FIG. 10.

In this particular configuration, an external force is applied to a lock cap 120 (similar to plunger 12, discussed above) to provide the compression of an included mechanical spring, and then the unlocking of this spring force to operate the included flux switch. As best shown in FIG. 11, locking cap 120 includes a set of pusher arms 122 that extend downward toward the location of the mechanical spring apparatus portion 111 of apparatus 100. Pusher arms 122 engage with a compression framework 124 surrounding an included mechanical spring 126, so that the application of an external force to locking cap 120 is directed through pusher arms 122 and compression framework 124 to compress mechanical spring 126. As will be discussed below in association with FIGS. 22-24, a mechanical lock configuration is used in this embodiment (instead of a magnetic lock as described above) to control the release of compressed mechanical spring 126.

A dual-core embodiment of the inventive energy harvesting apparatus offers several advantages over the above-described single-core embodiment. In particular, the use of the pair of cores 110, 112 allows for various types of bi-directional motion of the movable subassembly, including oscillations around an equilibrium point. As mentioned above, energy generation through oscillatory motion of coil 118 may be desirable in cases where all of the mechanical energy cannot be converted to electrical energy in a single cycle.

Figure 12:
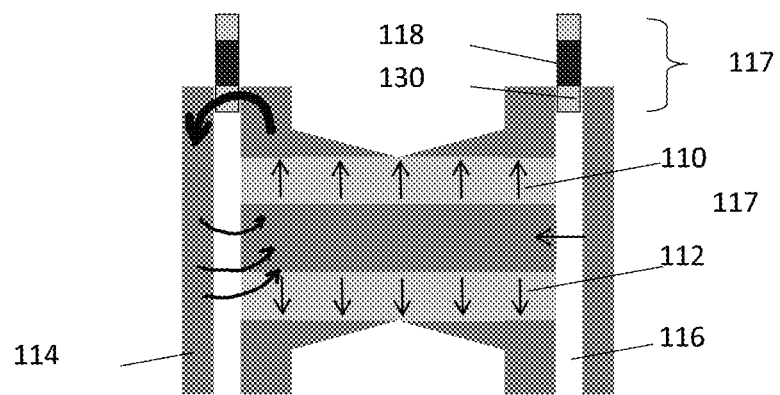
FIG. 12 illustrates an initial state of the flux switch portion of the dual-core embodiment shown in FIGS. 10 and 11.

FIGS. 12-20 are simplified diagrams showing the evolution of induced current flow through both first magnetic core 110 and second magnetic core 112 in accordance with dual-core apparatus 100 of FIG. 10. For the sake of simplicity, only the movement of coil subassembly 117 with respect to the dual-core configuration is shown in FIGS. 12-20, which illustrate the changes in captured flux as coil 118 moves across each core in sequence. The initial state of the flux switch is shown in FIG. 12, where movable subassembly is positioned above shell 114 such that coil 118 is completely withdrawn. Thus, none of the magnetic flux is captured by coil 118, as indicated by the magnetic field lines circling through ferromagnetic shell 114, magnetic core 110 and ferromagnetic plug 134.

Figure 13:
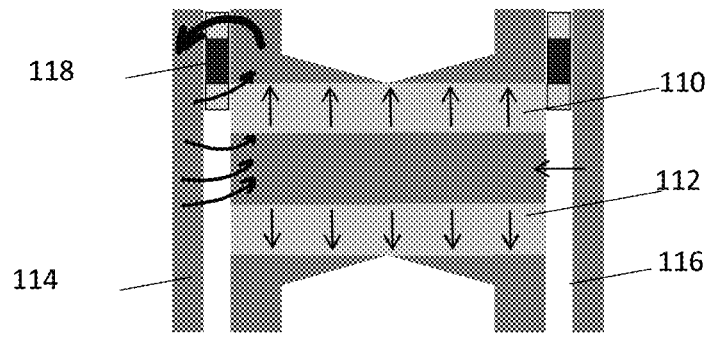
FIG. 13 depicts a following state of the dual-core flux switch, with the motion of the electrical coil toward a top core of the top/bottom configuration.
Figure 14:
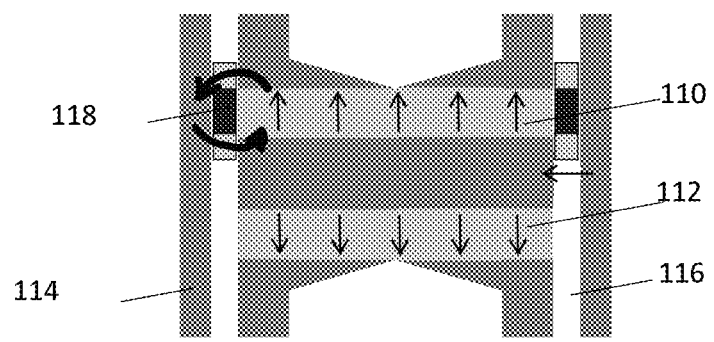
FIG. 14 illustrates the flux switch of the dual-core configuration at the point in the process where the electrical coil is aligned with the top magnetic core.

FIG. 13 shows a following step where coil 118 moves downward toward first magnetic core 110 and begins to capture a portion of its magnetic flux. This change in captured flux thus initiates the flow of an induced current through coil 118. The captured flux density continues to increase as coil 118 moves further downward into alignment with first magnetic core 110, as shown in FIG. 14. The continuing change in flux density thus maintains the circulation of the induced current within coil 118.

Figure 15:
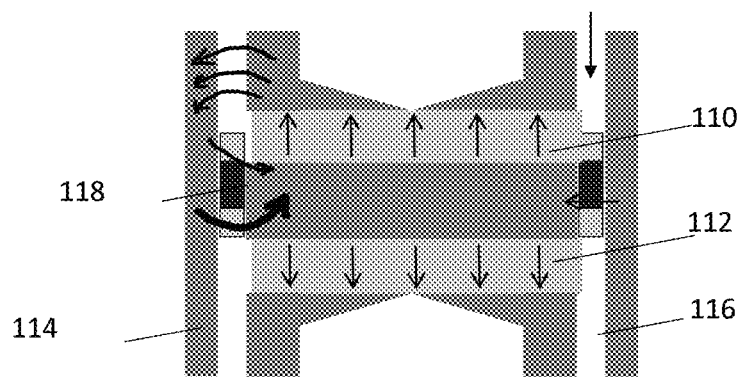
FIG. 15 shows the continued downward movement of the electrical coil, and reduction in captured flux as the coil moves away from the top magnetic core.
Figure 16:
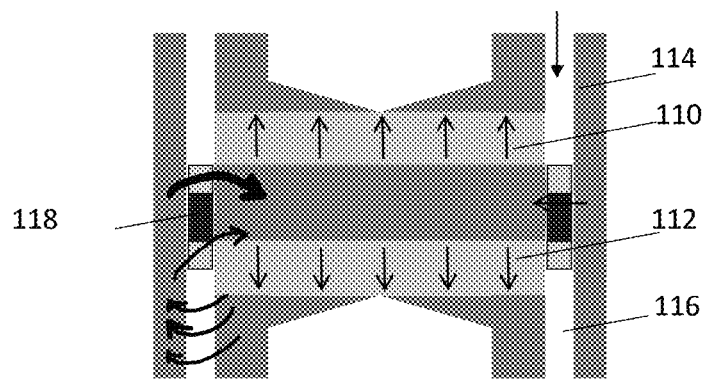
FIG. 16 illustrates the point in the process where the electrical coil begins to interact with the bottom magnetic core, illustrating the reversal of the flux based on the opposite orientation of the bottom magnetic core.
Figure 17:
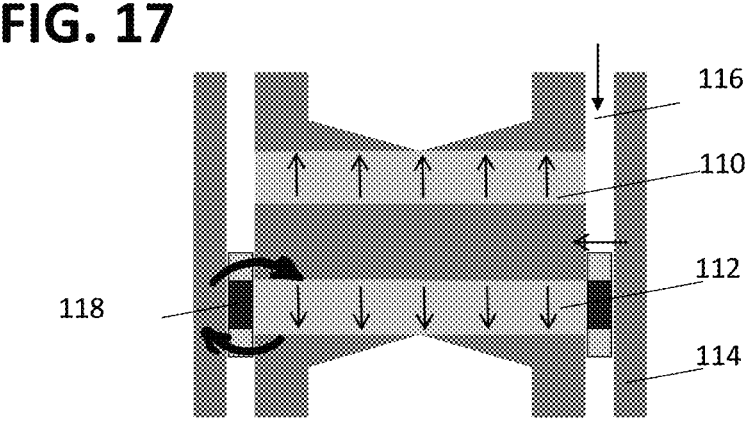
FIG. 17 shows the continued movement of the electrical coil toward the bottom magnetic core, illustrating an increase in flux.
Figure 18:
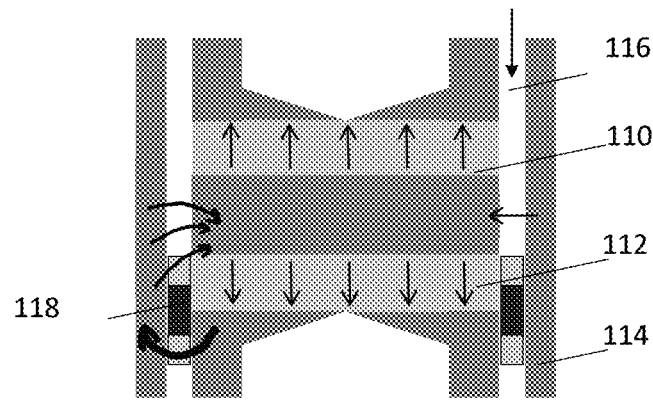
FIG. 18 illustrates a following point in time where the electrical coil is aligned with the bottom core.
Figure 19:
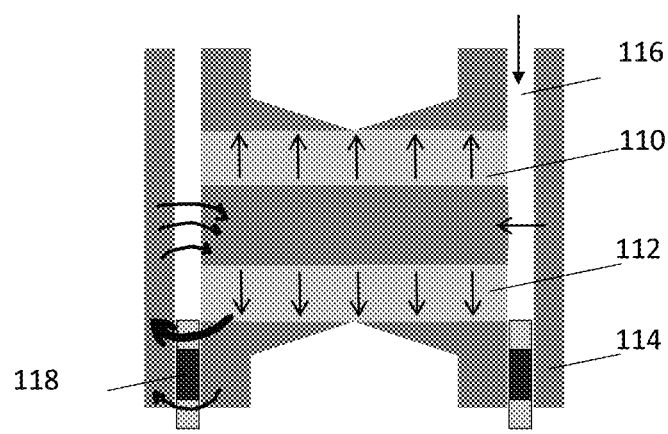
FIG. 19 illustrates a following time where the electrical coil is moving away from the bottom magnetic core, decreasing the amount of flux captured by the coil.
Figure 20:
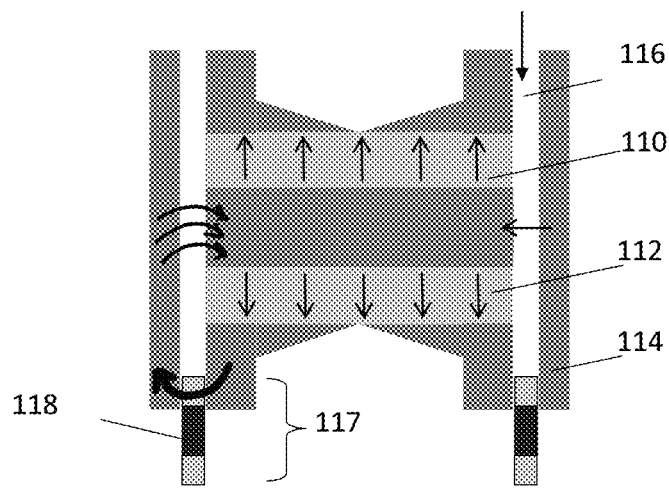
FIG. 20 shows an end of an exemplary energy harvesting cycle, where the electrical coil moves out of the reach of the flux created by the bottom magnetic core.

As coil 118 continues to move downward and away from first magnetic core 110, the flux captured by coil 118 starts to decrease, as indicated by the diagram in FIG. 15. Depending on the spacing between first magnetic core 110 and second magnetic core 112, there may be a point in the cycle where coil 118 no longer in position to interact with the flux created by either core. Following, as soon as coil 118 begins to interact with second magnetic core 112, the direction of the flux switches as shown in FIG. 16, where this abrupt change causes a spike in the induced electrical current. In similar fashion, as coil 118 continues its relative motion with respect to second magnetic core 112, the amount of captured flux will continue to change, and the induced current will continue to flow within coil 118, as depicted in the diagrams of FIGS. 17-20.

Figure 21:
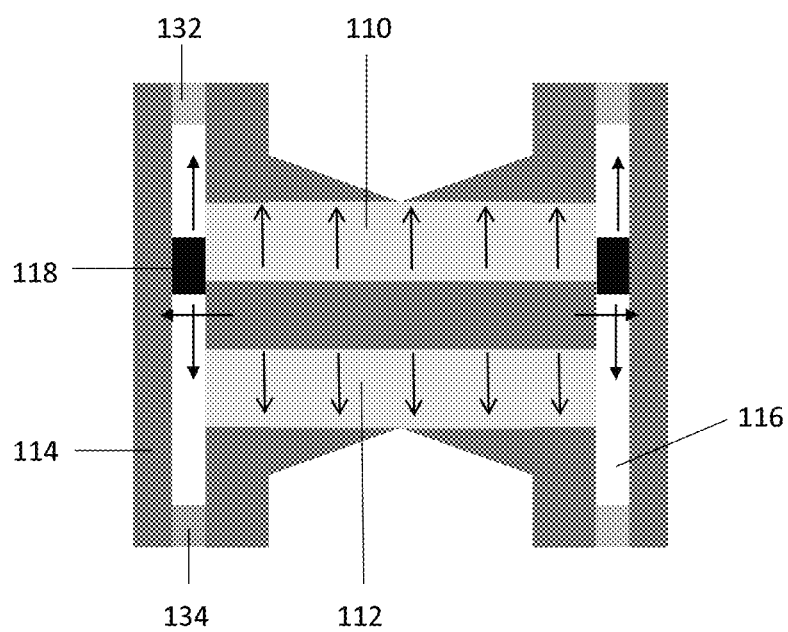
FIG. 21 illustrates an alternative configuration of the dual-core embodiment, where in this case the magnetic plugs are permanently fixed to the top and bottom surfaces of the ferromagnetic shell within which the electrical coil moves with respect to the magnetic core.

As with the single-core embodiment, there are several different configurations of the dual-core embodiment that may be utilized to simplify its design, albeit at a cost of reduced energy generation. One exemplary embodiment in shown in FIG. 21, where magnetic switch plugs 120, 122 are permanently fixed within the terminations of trench 116 in shell 114.

Figure 22:
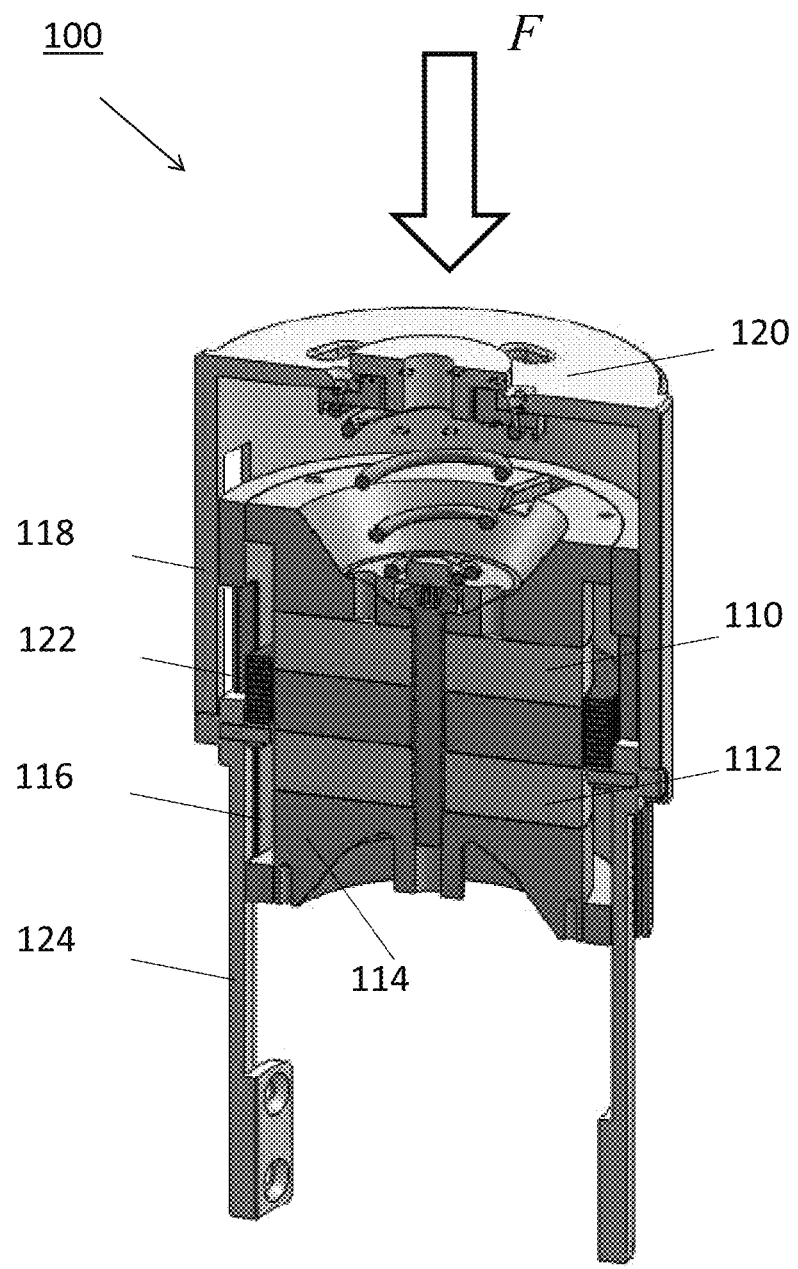
FIG. 22 shows a first position of an exemplary mechanical lock configuration that can be used to control the release of the compressed mechanical spring in accordance with the principles of the present invention.
Figure 23:
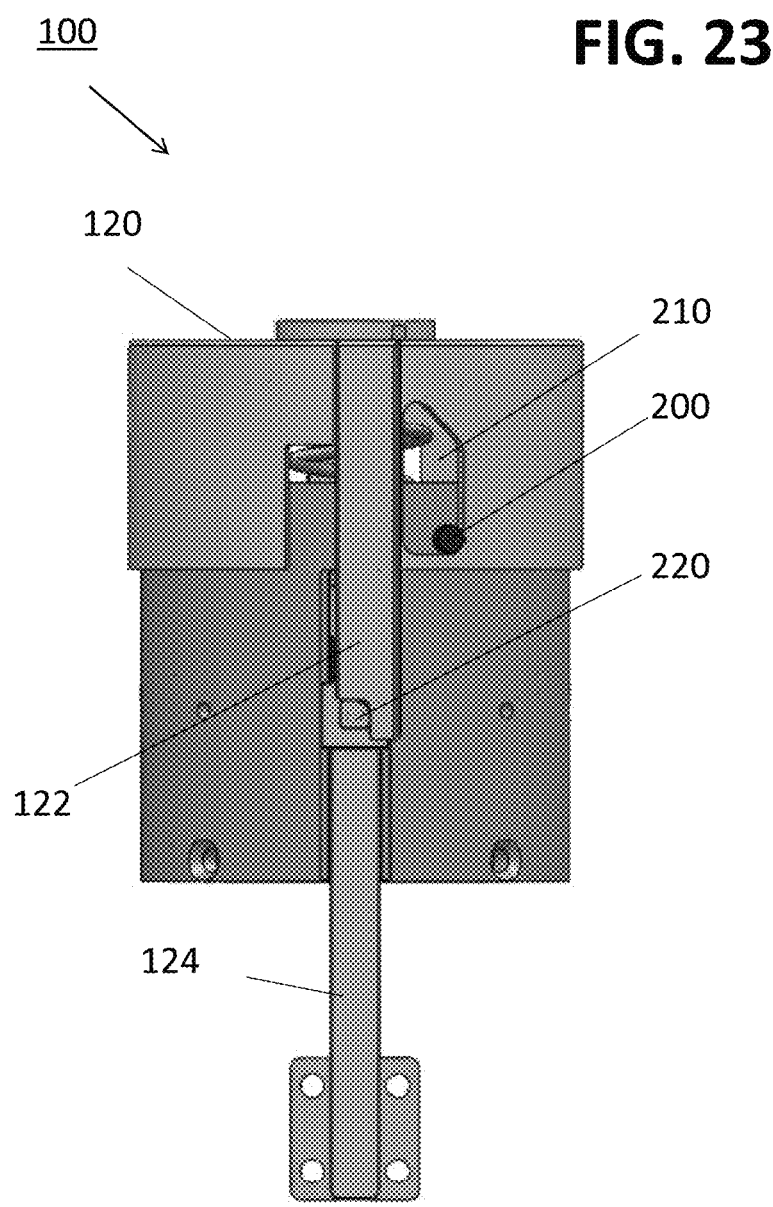
FIG. 23 shows an intermediate position of the mechanical lock, as the cap is rotated.
Figure 24:
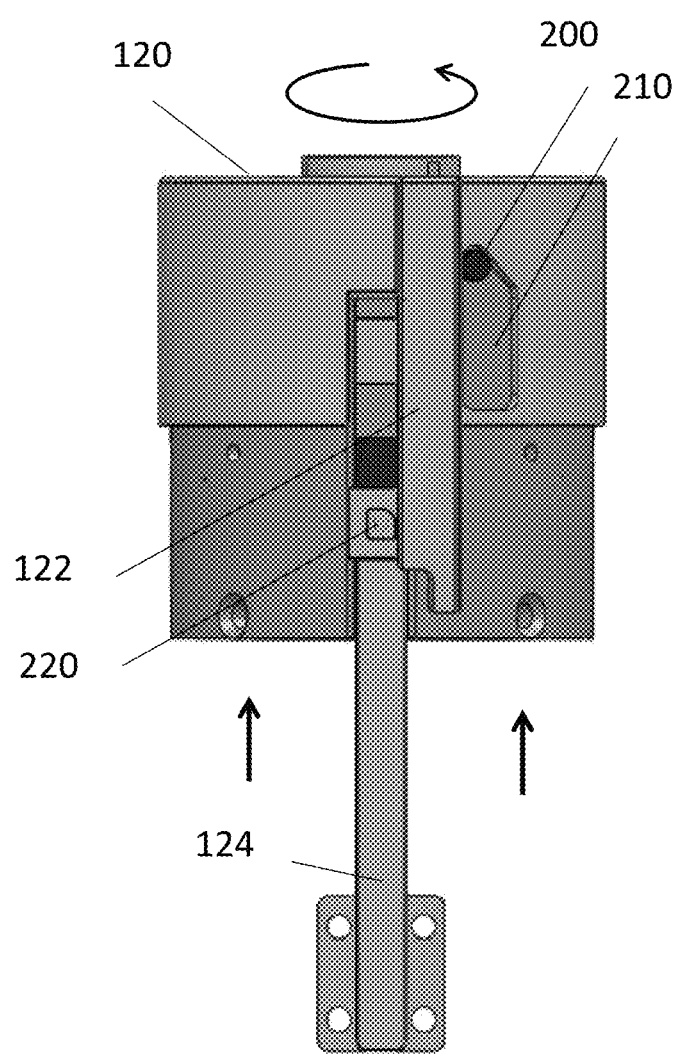
FIG. 24 shows a final position of the mechanical lock (i.e., in the "unlocked" state) where the locking pins are disengaged and the mechanical spring is free to return to its initial position.

As mentioned above, the particular dual-core embodiment as shown in FIGS. 10 and 11 also illustrates the utilization of a mechanical "lock" configuration to control the release of mechanical spring 126 and initiate the movement of coil 118 with respect to first and second magnetic cores 110, 112. In this particular mechanical arrangement, as shown in FIGS. 22-24, a pair of lock pins 200 is formed on shell 114 (only one lock pin 200 being visible in the view of FIG. 22). Lock cap 120 is formed to include a pair of keying arrangements 212 that engage with the pair of lock pins 200. Compression frame 124 is shown as including pusher pins 214 that engage with pusher arms 122 in the manner shown in FIG. 22.

As an external force is applied to lock cap 120, its downward movement also causes attached pusher arms 122 to move downward as well. The engagement between pusher arms 122 and compression frame 124 function to transfer this applied force to mechanical spring 126, accumulating mechanical energy as the force is continued to be applied.

Indeed, as the application of an external force continues, the movement of lock pins 200 in keying arrangements 212 causes the rotation of lock cap 120, as shown in FIG. 24. The rotation of lock cap 120 disengages pusher pins 214 from pusher arms 122, thus "unlocking" the compressed mechanical spring and initiating the relative movement of coil 118 with respect to first and second magnetic cores 110, 112.

It is to be understood that this particular mechanical lock configuration is exemplary only, as is the magnetic lock configuration discussed above. Various other mechanisms may be used to control the compression and release of the mechanical spring within the apparatus of the present invention, and all are considered to fall within the scope of the invention as long as the mechanism allows for the movement of the spring to be translated into a movement of the electrical coil so as to create a change in the magnetic flux captured by the coil.

Figure 25:
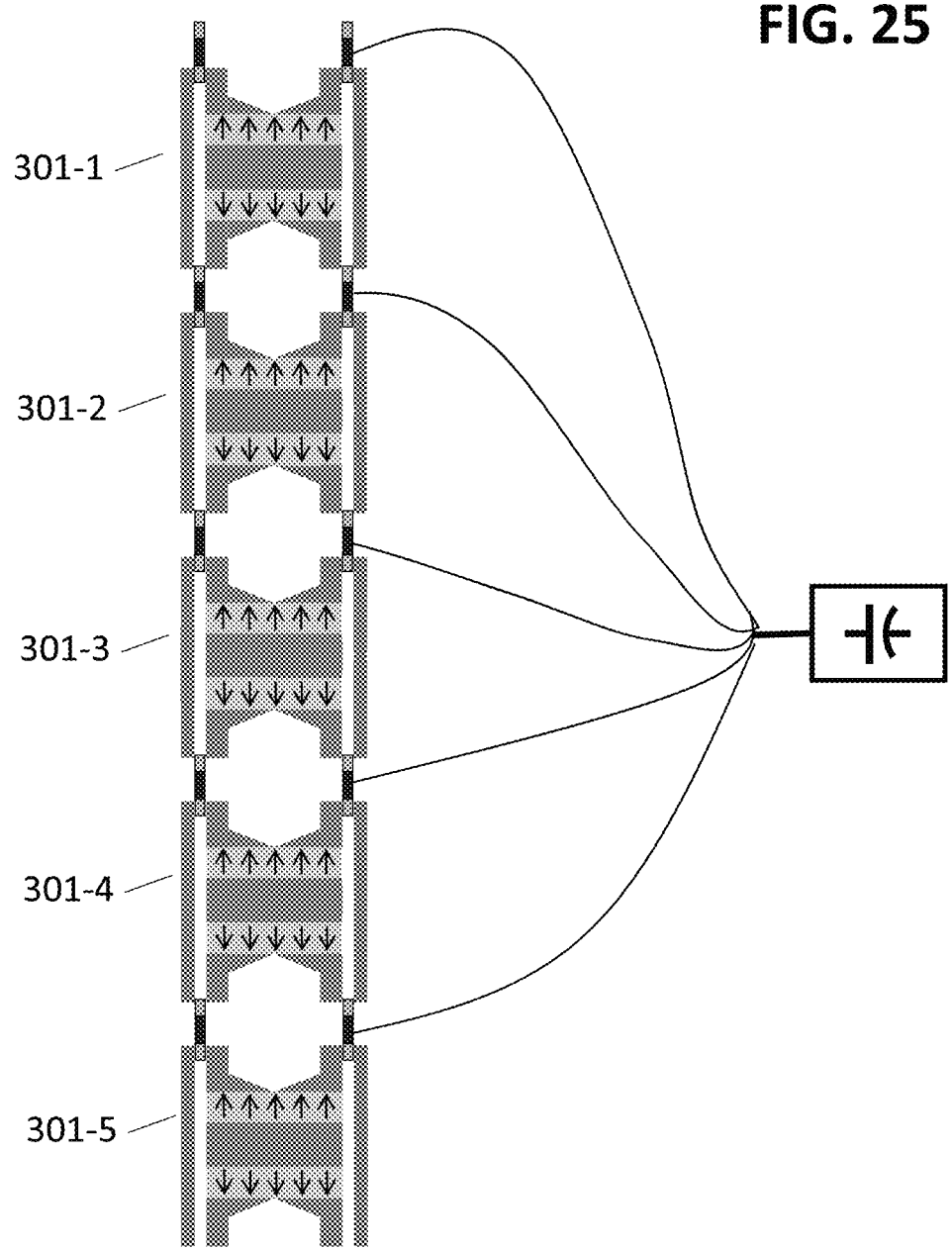
FIG. 25 illustrates yet another embodiment of the present invention, in this case comprising a multi-core structure formed of a multiple number of dual-core assemblies.

In some cases, the required mechanical displacement may be too large to be captured by either the single-core or dual-core embodiments described above. Thus, another embodiment of the present invention takes the form of a "multi-core" configuration, which consists of a plurality of dual-core units that are disposed in a linear array. FIG. 25 illustrates this concept, showing the movement of an exemplary coil 300 downward through a group of five dual-core units 310.

As mentioned above, the variable inductance magnetic flux switch energy harvester of the present invention is particularly suitable for use in situations where an applied force may be aperiodic. The movement of prosthetic lower limbs, as well as orthotic devices coupled to limbs, are exemplary situations where the obviously aperiodic type of human locomotive force applied to these prosthetic/orthotic devices is considered to be a good source of mechanical energy for harvesting in accordance with the principles of the present invention. FIGS. 26-30 illustrate various arrangements where a harvesting element of the present invention (for the sake of simplicity, shown in each illustration as a dual-core apparatus 100) may be utilized with a prosthetic limb. In general, it is to be understood that the movement of any type of prosthetic or orthotic device may be used to control the energy harvesting capability of an embodiment of the inventive apparatus that is co-located with the prosthetic or orthotic device.

FIG. 26 illustrates an exemplary embodiment 400 where dual-core mechanical energy harvesting apparatus 100 is utilized in conjunction with a separate prosthetic foot device 410. In this embodiment, energy harvesting apparatus 100 is activated by the movement of prosthetic foot device 410. The inclusion of energy harvesting apparatus 100 functions to accept downward-directed and/or upward-directed and/or rotational forces in the ankle area directly above foot device 410 and allows that force to be harvested as electrical energy in the manner described above. The harvested electrical energy may be used as a power source for electronic circuitry embedded within prosthetic foot device 410, for example.

Figure 28:
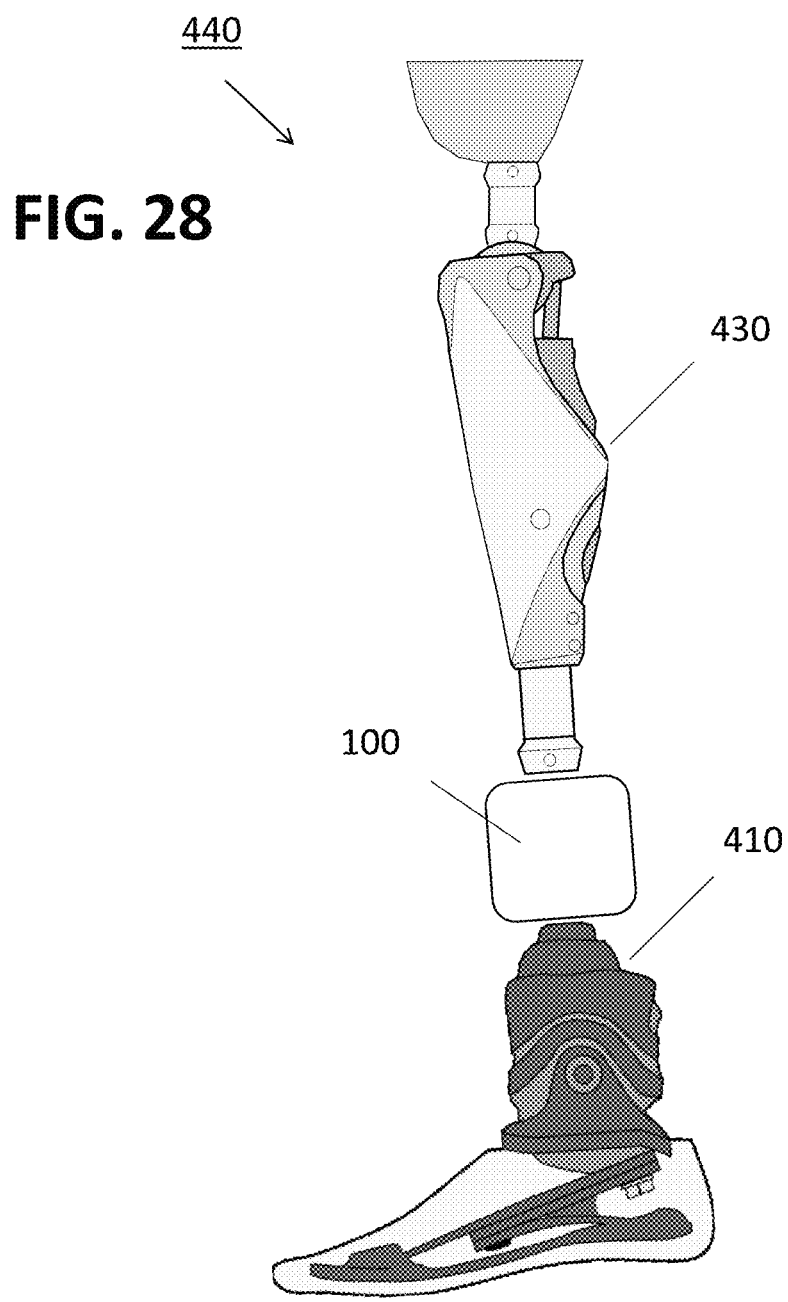
FIG. 28 illustrates an application of the inventive harvesting apparatus, where in this case the harvesting apparatus is used with, and positioned between, a prosthetic lower limb and a prosthetic foot device.

FIG. 27 shows an alternative embodiment 420, where dual-core mechanical energy harvesting device 100 is positioned underneath a prosthetic lower limb 430. As with embodiment 400 of FIG. 26, energy harvesting apparatus 100 is activated in this case by the movement of prosthetic lower limb 430. In this exemplary embodiment 420, energy harvesting device 100 is oriented such that downward-directed and/or upward-directed and/or rotational forces against the lower termination 432 of limb 430 initiates compression of the mechanical spring within apparatus 100 to being an energy harvesting cycle, as described above. FIG. 28 illustrates an embodiment 440 that comprises a combination of the configurations of FIGS. 26 and 27, where energy harvesting apparatus 100 is positioned between prosthetic foot device 410 and prosthetic lower limb 430. In this particular embodiment 440, energy harvesting device 100 is configured to convert mechanical energy associated with downward-directed and/or upward-directed and/or rotational forces into electrical energy.

Figure 29:
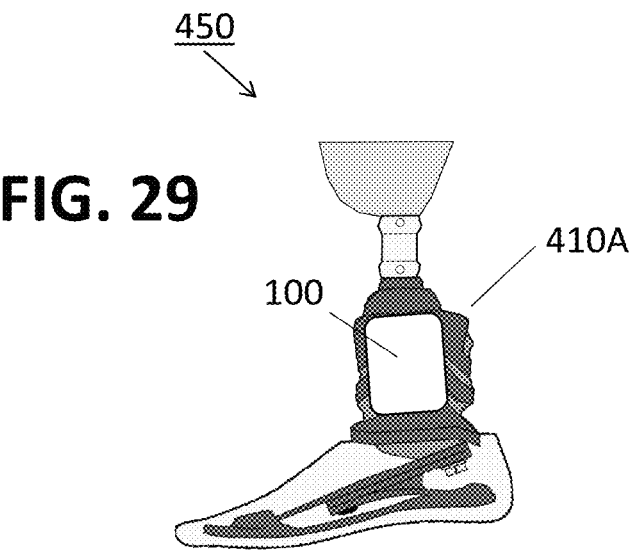
FIG. 29 illustrates an alternative to the application shown in FIG. 26, where in this case the inventive harvesting apparatus is integrated within to form part of the prosthetic foot device.
Figure 30:
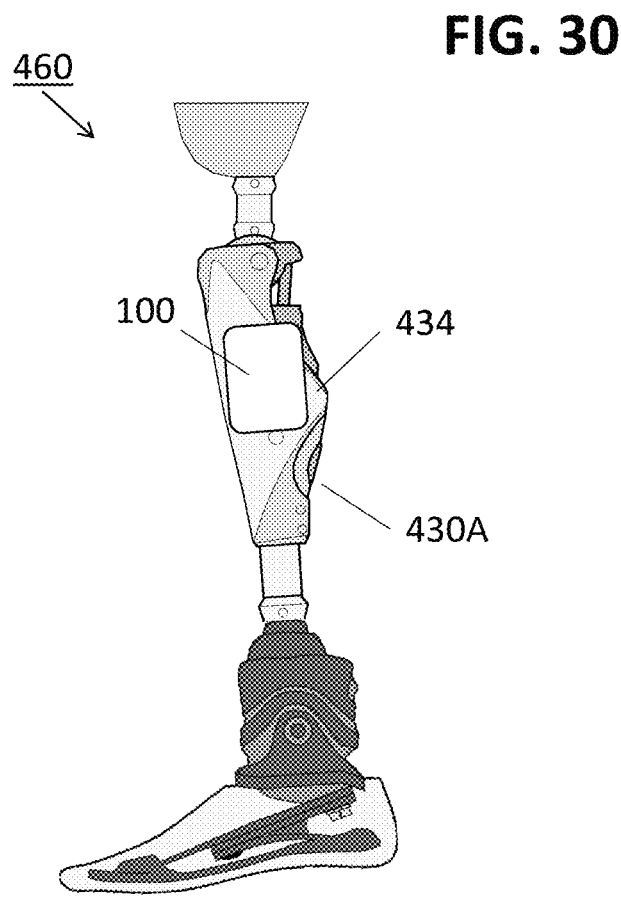
FIG. 30 illustrates an alternative to the application shown in FIG. 27, where in this case the inventive harvesting apparatus is integrated within to form part of the prosthetic lower limb.

FIGS. 29 and 30 illustrate some alternative embodiments of utilizing the inventive energy harvesting apparatus in combination with prosthetic devices. In this case, the exemplary dual-core mechanical energy harvesting device is directly incorporated within, and forms part of, the prosthetic/orthotic device itself. FIG. 29 illustrates an embodiment 450 where dual-core energy harvesting apparatus 100 is integrated within an exemplary prosthetic foot device 410A. FIG. 30 illustrates an embodiment 460 where dual-core energy harvesting apparatus 100 is disposed within a knee region 434 of an exemplary prosthetic lower limb 430A. Similar to the embodiments of FIGS. 26-28, the configurations shown in FIGS. 29 and 30 may utilize the harvested energy to power included electronics within the prosthetic devices. Again, it is to be understood that the inventive energy harvesting apparatus may be used to harvest electrical energy from the movement of orthotic devices, as well as prosthetic devices as illustrated in the above examples.

Summarizing, the present invention is directed to an apparatus and method for using the apparatus to provide mechanical-to-electrical energy conversion suitable in a wide range of environments, providing effective coupling to a broad range of forces and displacements that are often not accessible by conventional energy harvesting configurations that rely on high frequency, large amplitude mechanical motion as the mechanical energy source. To achieve the mechanical-to-electrical conversion in accordance with the principles of the present invention, a mechanical energy storage device in the form of a mechanical spring is combined with a variable inductance magnetic flux switch, where the activation of the spring causes a rapid change in the magnetic flux penetrating the electrical coil within the switch. Various embodiments may utilize a single magnetic core, a dual-core arrangement, or even a multi-core arrangement to provide a longer range of motion for the movement of the mechanical spring.

Figure 31:
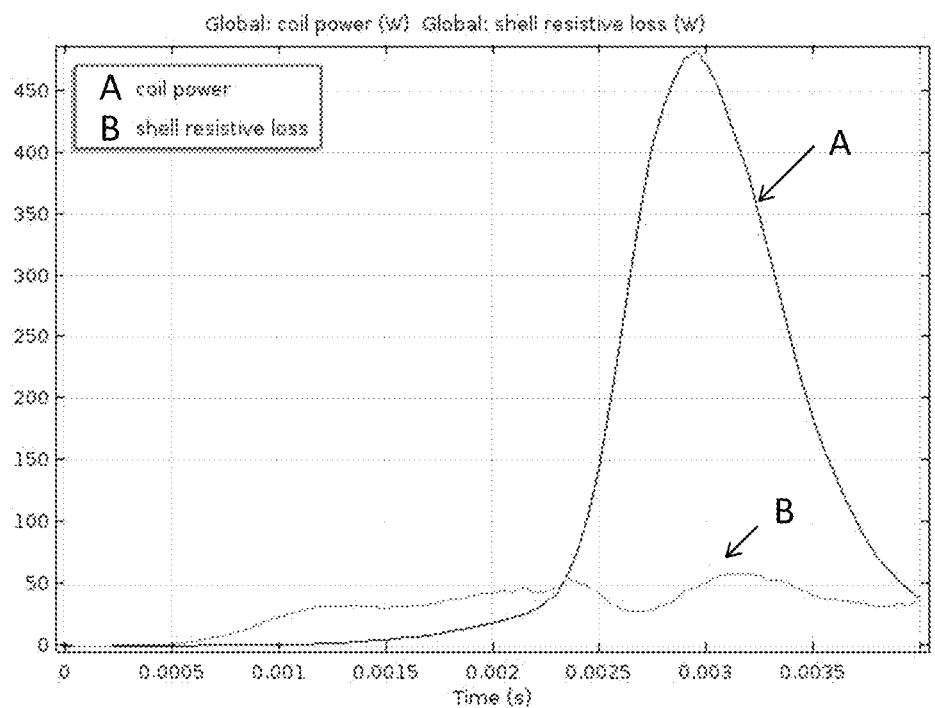
FIG. 31 contains plots showing exemplary results of power generated by a single-core embodiment of the mechanical energy harvesting apparatus of the present invention.
Figure 32:
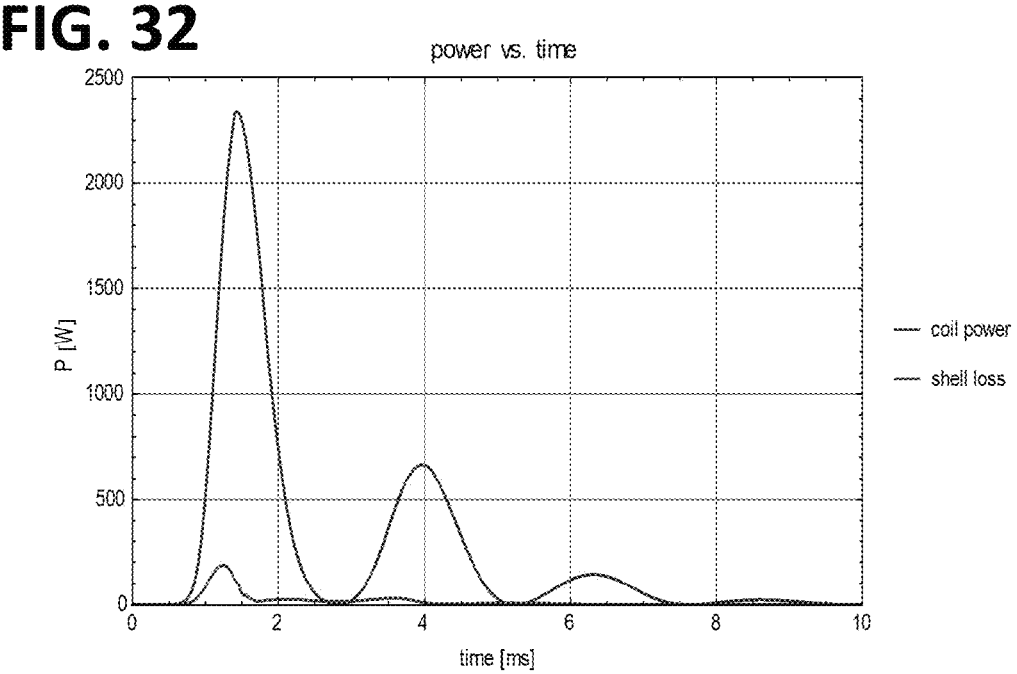
FIG. 32 contains plots showing exemplary results of power generated by a dual-core embodiment of the mechanical energy harvesting apparatus of the present invention.

Indeed, useful amounts of power are expected to be generated using various embodiments of the present invention. FIG. 31 is a plot of computed results for power generated by the single-core embodiment of the present invention as shown in FIGS. 1-9. Plot A in FIG. 31 shows the total power generated by coil 32 (over hundreds of watts), with the eddy current losses associated with shell 26 shown in plot B. FIG. 32 shows similar plots for the dual-core embodiment, where the pair of peaks in the generated power are expected as the coil achieves maximum change in flux at two separate points in time as it passes by each of the magnetic cores.

The present invention, which is disclosed herein, is not to be limited by the embodiments described or illustrated herein, which are given by way of example and not of limitation. Other embodiments of the present invention will be apparent to those skilled in the art from a consideration of the instant disclosure, or form practice of the present invention. Various omissions, modifications, and changes to the principles disclosed herein may be made by one skilled in the art without departing from the true scope and spirit of the present invention, which is indicated by the following claims.

What is claimed is:

1. Apparatus for harvesting electrical energy from mechanical energy associated with mechanical motion, comprising
a mechanical spring disposed within a housing;
a variable inductance magnetic flux switch positioned within an open central area of the housing, the variable inductance magnetic flux switch comprising
a stationary magnetic core component;
a movable electrical coil subassembly disposed to surround the stationary magnetic core component, the movable electrical coil subassembly coupled to the mechanical spring in a manner such that movement of the mechanical spring provides movement of the electrical coil subassembly with respect to the stationary magnetic core component; and a plunger disposed over the combination of the stationary magnetic core component and the movable electrical coil subassembly, the plunger responsive to an application of an external force to move the variable inductance magnetic flux switch downward and into the housing, compressing the mechanical spring disposed therein; and a spring lock mechanism for releasing the mechanical spring when in a compressed state, providing movement of the mechanical spring and coupled electrical coil subassembly, wherein a spring-controlled movement of the electrical coil subassembly with respect to the stationary magnetic core changes both the coil inductance and the magnetic flux captured by the electrical coil subassembly, thereby creating a flow of electrical current for storage as the output of the apparatus as long as the electrical coil subassembly continues to move with respect to the stationary magnetic core.

2. The apparatus as defined in claim 1 wherein the apparatus further comprises a ferromagnetic shell for encasing the stationary magnetic core component, the ferromagnetic shell providing a path for magnetic flux to be created within the variable inductance magnetic flux switch.

3. The apparatus as defined in claim 2 wherein the ferromagnetic shell is formed to include a trench in a spaced-apart relationship with the stationary magnetic core component, wherein the movable electrical coil subassembly is disposed within the trench and the spring-controlled movement of the electrical coil subassembly within the trench creates a change in relative position between the electrical coil subassembly and the ferromagnetic shell encasing the stationary magnetic core component, changing both the captured magnetic flux and electrical coil inductance, creating the flow of electrical current through the electrical coil subassembly.

4. The apparatus as defined in claim 2 wherein the movable electrical coil subassembly comprises an electrical coil held within a support member.

5. The apparatus as defined in claim 4 wherein the movable electrical coil subassembly further comprises a pair of ferromagnetic rings disposed below and above the electrical coil, the pair of ferromagnetic rings forming a magnetic switch component when in proximity to the ferromagnetic shell, forming a magnetic flux path therewith.

6. The apparatus as defined in claim 4 wherein
the support member comprises a ferromagnetic lock plate disposed above the electrical coil and extending over the mechanical spring such that the movement of the plunger causes the support member to move and compress the mechanical spring, the ferromagnetic lock plate magnetically attracted to the ferromagnetic shell; and
the spring lock mechanism comprises a magnetic lock including a mechanical stop that engages with the ferromagnetic lock plate upon compression of the mechanical spring, overcoming the magnetic attraction between the ferromagnetic lock plate and the ferromagnetic shell so as to release the mechanical spring and initiate movement of the mechanical spring and electrical coil subassembly with respect to the stationary magnetic core component.

7. The apparatus as defined in claim 4 wherein the spring lock mechanism comprises a mechanical lock including a pusher coupled to the plunger and locking pins disposed on an outer surface of the ferromagnetic shell, the locking pins engaging keyways formed on the plunger to release the mechanical spring upon reaching a fully compressed state.

8. The apparatus as defined in claim 1 wherein the stationary magnetic core component comprises a single permanent magnet.

9. The apparatus as defined in claim 1 wherein the stationary magnetic core component comprises at least one pair of permanent magnets, disposed in a spaced-apart relationship and positioned in an oppositely-poled arrangement.

10. The apparatus as defined in claim 9 wherein the stationary magnetic core component comprises a plurality of pairs of permanent magnets, aligned in a manner such that the movable electrical coil subassembly moves along the plurality of pairs of permanent magnets, under the control of the movement of the coupled mechanical spring.

11. The apparatus as defined in claim 1 wherein the apparatus further comprises a return spring disposed below the variable inductance magnetic flux switch, the return spring responding to a removal of an external force to move the plunger into its original location.

12. A method of harvesting electrical energy from mechanical movement, comprising
providing a variable inductance magnetic switch including a stationary magnetic core component and a movable electrical coil subassembly disposed to surround the stationary magnetic core component;
providing a mechanical spring coupled to the movable electrical coil; and
impressing a force on the coupled mechanical spring and movable electrical coil so as compress the mechanical spring; and
unlocking the compressed mechanical spring to cause movement of the released mechanical spring and coupled electrical coil subassembly, where the movement of the electrical coil subassembly with respect to the stationary magnetic core changes both the coil inductance and the magnetic flux captured by the electrical coil subassembly so as to create a flow of electrical current therethrough.

13. The method as defined in claim 12 wherein the unlocking step comprises a magnetic unlocking through the application of a force sufficient to overcome a magnetic attraction between a ferromagnetic shell encasing the stationary magnetic core component and a ferromagnetic lock plate disposed over the combination of the mechanical spring and the movable electrical coil subassembly.

14. The method as defined in claim 12 wherein the unlocking step comprises a mechanical unlocking through the application of a force sufficient to disengage a housing supporting the mechanical spring from a ferromagnetic shell encasing the stationary magnetic core component, allowing a compressed mechanical spring movement to also move the electrical coil subassembly with respect to the stationary magnetic core component.

15. A system for converting mechanical energy to electrical energy for powering an associated prosthetic or orthotic device, the system comprising
a mechanical spring; and
a variable inductance magnetic flux switch, the variable inductance magnetic flux switch comprising
a stationary magnetic core component;

a movable electrical coil subassembly coupled to the mechanical spring in a manner such that movement of the mechanical spring by the associated prosthetic or orthotic device also provides movement of the electrical coil subassembly; and a spring lock mechanism for releasing the mechanical spring when in a compressed state, providing movement of the mechanical spring and coupled electrical coil subassembly, where the movement of the electrical coil subassembly with respect to the stationary magnetic core changes both the coil inductance and the magnetic flux captured by the electrical coil subassembly, thereby creating a flow of electrical current for powering the associated prosthetic or orthotic device.

16. The system as defined in claim 15 wherein the mechanical spring is disposed within a housing;

the variable inductance magnetic flux switch is positioned within an open central area of the housing, the movable electrical coil subassembly is disposed to surround the stationary magnetic core, and the system further comprises a plunger disposed over the combination of the stationary magnetic core component and the moveable electrical coil subassembly, the plunger responsive to an application of an external force by the associated prosthetic or orthotic device to move the variable inductance magnetic flux switch downward and into the housing, compressing the mechanical spring disposed therein.

17. The system as defined in claim 15 wherein the system is formed as a stand-alone component disposed in a mechanical relationship within the prosthetic or orthotic device.

18. The system as defined in claim 15 wherein the system is integrated within and forms part of the prosthetic or orthotic device.

19. The system as defined in claim 15 wherein the prosthetic or orthotic device comprises a prosthetic foot device.

20. The system as defined in claim 15 wherein the prosthetic or orthotic device comprises a prosthetic lower limb device.

21. The system as defined in claim 15 wherein the prosthetic or orthotic device comprises a combination of a prosthetic foot device and a prosthetic lower limb device.

* * * * *